Figure 1:
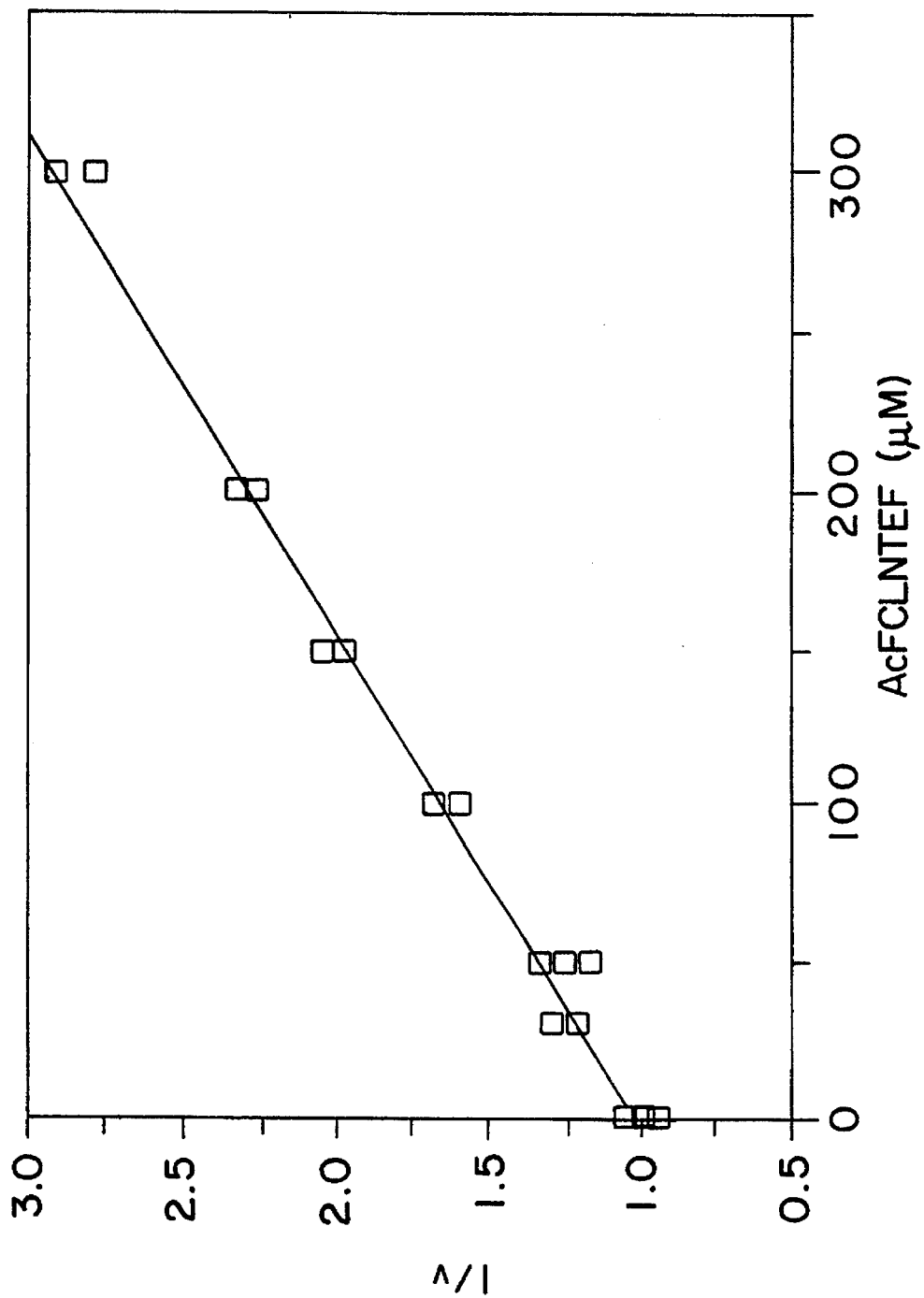

United States Patent [19]
Cooperman et al.

[11] Patent Number: 5,459,063
[45] Date of Patent: Oct. 17, 1995

[54] PLASMODIUM FALCIPARUM RIBONUCLEOTIDE REDUCTASE DNA

[75] Inventors: Barry S. Cooperman, Penn Valley; Harvey Rubin, Philadelphia; Jerome Salem, Cheltenham; Alison L. Fisher, Blue Bell, all of Pa.

[73] Assignee: The University of Pennsylvania, Philadelphia, Pa.

[21] Appl. No.: 136,743

[22] Filed: Oct. 14, 1993

[51] Int. Cl.$^6$ .............................. C12N 9/02; C12N 15/53
[52] U.S. Cl. .................. 435/252.3; 435/189; 435/320.1; 536/23.2
[58] Field of Search .................. 536/23.2; 435/189, 435/320.1, 252.3

[56] References Cited

FOREIGN PATENT DOCUMENTS

| 0383190 | 8/1990 | European Pat. Off. . |
| 493770A2 | 8/1992 | European Pat. Off. . |

OTHER PUBLICATIONS

D. Chakrabarti et al., *Proceedings of the National Academy of Science USA*, vol. 90, issued Dec. 1993 "Cloning and characterization of subunit genes of ribonucleotide reductase, a cell-cycle-regulated enzyme, from *Plasmodium falciparum*", pp. 12020–12024.
H. Rubin et al., *Proceedings of the National Academy of Science USA*, vol. 90, issued Oct. 1993 "Cloning, sequence determination, and regulation of the ribonucleotide reductase subunits from *Plasmodium falciparum*: A target for antimalarial therapy", pp. 9280–9284.
C. T. Atkinson et al., *American Journal of Tropical Medicine and Hygeine*, vol. 45, No. 5, issued Nov. 1991 "Stage–specific untrastructural effects of desferrioxamine on *Plasmodium falciparum* in vitro" pp. 593–601.
Yang et al., *FEBS Lett.* 272, 61–64 (1990).
Paradis et al., *J. Biol. Chem.* 263, No. 31, 16045–16050 (1988).
Cosentino et al., *Biochem. Cell. Biol.* 69, 79–83 (1991).
Mann et al., *Biochemistry* 30, 1939–1947 (1991).
Pavloff et al., *J. DNA Seq. Mapping* 2, 227–234 (1992).
Chang et al., *Int. J. Pept. Protein Res.*, 246–249 (1978).
Meienhofer et al., *Int. J. Pept. Protein Res.*, 35–42 (1979).
*Science* 256, 1135 (1992).
Miller, *Science* 257, 36–37 (1992).
Salem et al., *FEBS Lett.* 323, 1,2, 93–95 (1993).
Reichard, *Science* 260, 1773–1777 (1993).
Lammers et al., *Structure and Bonding* 54, 64–82 (1983).
McClements et al., *Virology* 162, 270–273 (1988).
Gaudreau et al., *J. Med. Chem.* 33, 723–730 (1990).
Stubb, *Adv. Enzymol. Relat. Areas Mol. Biol.* 63, 349–419 (1990).
Eriksson et al., *J. Biol. Chem.* 261, 1878–1882 (1986).
Paradis, et al., *Int. J. Pep. Prot. Res.*, vol. 37, 72–79 (1990).
Chang, et al., *Bio & Med. Chem. Lett.*, vol. 2, 1207–1212, (1992).
Krogsrud, et al., *Anal. Biochem.* 213, 386–394 (1993).
Gaudreau et al.,*J. Med. Chem.* 85, 346–350 (1992).

*Primary Examiner*—Robert A. Wax
*Assistant Examiner*—Keith D. Hendricks
*Attorney, Agent, or Firm*—Seidel Gonda Lavorgna & Monaco

[57] ABSTRACT

This invention relates to the ribonucleotide reductase of *Plasmodium falciparum* (Pf RR), to the subunits of Pf RR (Pf R1 and Pf R2), and to compounds comprising peptides derived from the Pf R2 C-terminus sequence that inhibit the action of protozoal RR. The invention provides a method for the prevention and treatment of malaria caused by *P. falciparum* by controlling the proliferation of *P. falciparum* comprising administering to a patient at least one peptide according to the invention. Antimalarial compositions are provided which comprise a pharmaceutically acceptable carrier and at least one peptide according to the invention which inhibits the *P. falciparum* ribonucleotide reductase reduction of ribonucleotides to 2'-deoxyribonucleotides. Also provided are methods for diagnosing malaria and for screening potential antimalarial agents.

8 Claims, 1 Drawing Sheet

5,459,063

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
      ( A ) LENGTH: 1112 nucleotides
      ( B ) TYPE: nucleic acid
      ( C ) STRANDEDNESS: single
      ( D ) TOPOLOGY: linear ( x i ) SEQUENCE DESCRIPTION: SEQ ID NO:1:

```
TCTAGAATCC  AATATTTAGC  AAACAGGAAA  GAGAATTTAG  TGATTTACAA    50
AAAGGGAAAG  AGATAAATGA  GAAGAATTTT  AAATAAAGAG  AGTGATCGAT   100
TTACTTTATA  TCCAATATTA  TATCCTGATG  TTTTCCCATT  TTACAAGAAA   150
GCTGAAGCTA  GTTTTTGGAC  AGCAGAAGAA  ATTGATTATT  CTAGTGATTT   200
AAAAGATTTT  GAGAAATTGA  ATGAAAATGA  GAAACATTTT  ATAAAGCATG   250
TGTTAGCATT  TTTTGCAGCA  AGTGATGGTA  TAGTCTTAGA  GAATTTGGCA   300
GTAAGTTTTT  TAAGAGAGGT  TCAAATAACA  GAAGCTAAAA  AATTTTATTC   350
CTTTCAAATA  GCTGTAGAAA  ATATTCATTC  AGAAACATAT  AGTTTATTAA   400
TTGATAATTA  TATTAAAGAT  GAAAAGAAA   GATTAAATTT  ATTTCATGCT   450
ATAGAAAATA  TCCCTGCCGT  AAAAAATAAA  GCATTATGGG  CAGCAAAATG   500
GATTAACGAT  ACTAATTCGT  TTGCTGAAAG  AATTGTTGCT  AATGCATGTG   550
TTGAAGGAAT  ATTATTCAGT  GGTAGTTTTT  GTGCAATTTT  TTGGTTTAAG   600
AAACAAAATA  AATTACACGG  TTTGACATTT  AGTAATGAAT  TAATAAGTAG   650
AGATGAAGGA  CTACATACAG  ATTTTAATTG  CTTAATTTAT  AGTTTATTAG   700
ATAATAAACT  TCCAGAACAA  ATGGTACAAA  ATATTGTTAA  AGAAGCGGGG   750
GGTGTAGAAG  TTGAAAAGTC  TTTTATATGT  GAATCCTTAC  CATGTGATTT   800
AATAGGTATG  AATTCTAGAC  TTATGTCTCA  ATATATAGAA  TTTGTTGCTG   850
ATAGATTATT  AGAATGCTTA  GGATGCTCTA  AAATTTTCCA  TTCCAAAAAT   900
CCATTTAATT  GGATGGACTT  AATTTCACTT  CAAGGAAAAA  CAAACTTTTT   950
TGAGAAAAGA  GTCGCAGATT  ATCAAAAATC  AGGAGTCATG  GCTCAACGAA  1000
AGGATCATGT  CTTTGTCTG   AATACGGAAT  TTTAAATGAT  ACTCGAAATA  1050
TTTATTATAC  CATATGTATA  CTATATAAAT  ATATATATTA  AATAATGATA  1100
GTATTTTTTT  TT          1112
```

( 2 ) INFORMATION FOR SEQ ID NO:2:

( i ) SEQUENCE CHARACTERISTICS:
        ( A ) LENGTH: 322 amino acids
        ( B ) TYPE: amino acid
        ( D ) TOPOLOGY: linear ( x i ) SEQUENCE DESCRIPTION: SEQ ID NO:2:

```
Met Arg Arg Ile Leu Asn Lys Glu Ser Asp Arg Phe Thr Leu Tyr
                  5                  10                 15
Pro Ile Leu Tyr Pro Asp Val Phe Pro Phe Tyr Lys Lys Ala Glu
                 20                  25                 30
Ala Ser Phe Trp Thr Ala Glu Glu Ile Asp Tyr Ser Ser Asp Leu
                 35                  40                 45
Lys Asp Phe Glu Lys Leu Asn Glu Asn Glu Lys His Phe Ile Lys
                 50                  55                 60
His Val Leu Ala Phe Phe Ala Ala Ser Asp Gly Ile Val Leu Glu
                 65                  70                 75
Asn Leu Ala Val Ser Phe Leu Arg Glu Val Gln Ile Thr Glu Ala
                 80                  85                 90
Lys Lys Phe Tyr Ser Phe Gln Ile Ala Val Glu Asn Ile His Ser
                 95                 100                105
Glu Thr Tyr Ser Leu Leu Ile Asp Asn Tyr Ile Lys Asp Glu Lys
                110                 115                120
Glu Arg Leu Asn Leu Phe His Ala Ile Glu Asn Ile Pro Ala Val
                125                 130                135
Lys Asn Lys Ala Leu Trp Ala Ala Lys Trp Ile Asn Asp Thr Asn
                140                 145                150
Ser Phe Ala Glu Arg Ile Val Ala Asn Ala Cys Val Glu Gly Ile
                155                 160                165
Lys Phe Ser Gly Ser Phe Cys Ala Ile Phe Trp Phe Lys Lys Gln
                170                 175                180
Asn Lys Leu His Gly Leu Thr Phe Ser Asn Glu Leu Ile Ser Arg
                185                 190                195
Asp Glu Gly Leu His Thr Asp Phe Asn Cys Leu Ile Tyr Ser Leu
                200                 205                210
Leu Asp Asn Lys Leu Pro Glu Gln Met Val Gln Asn Ile Val Lys
                215                 220                225
Glu Ala Gly Gly Val Glu Val Glu Lys Ser Phe Ile Cys Glu Ser
                230                 235                240
Leu Pro Cys Asp Leu Ile Gly Met Asn Ser Arg Leu Met Ser Gln
                245                 250                255
Thr Ile Glu Phe Val Ala Asp Arg Leu Leu Glu Cys Leu Gly Cys
                260                 265                270
Ser Lys Ile Phe His Ser Lys Asn Pro Phe Asn Trp Met Asp Lys
                275                 280                285
Ile Ser Leu Gln Gly Lys Thr Asn Phe Phe Glu Lys Arg Val Ala
                290                 295                300
Asp Tyr Gln Lys Ser Gly Val Met Ala Gln Arg Lys Asp His Val
                305                 310                315
Phe Cys Leu Asn Thr Glu Phe
                320
```

( 2 ) INFORMATION FOR SEQ ID NO:3:

(i) SEQUENCE CHARACTERISTICS:
  (A) LENGTH: 2663 nucleotides
  (B) TYPE: nucleic acid
  (C) STRANDEDNESS: single
  (D) TOPOLOGY: linear (xi) SEQUENCE DESCRIPTION: SEQ ID NO:3:

```
GAGTACATCA GGAGATTAAG TGATGATGGT ATAAGGACCC CATCAGGTAA   50
ACCTATACAA ACAATGTATG TGTTGAATAG AAAGGGAGAA GAAGAAGATA  100
TATCCTTTGA TCAAATTTTA AAAAGAATAC AAAGGTTATC ATATGGTCTT  150
CATAAATTAG GTGAGTATCC TGCTTGTGTT ACACAAGGTG TAATCAATGG  200
GATGTATAGT AGTATAAAAA CCTGTGAATT AGATGAATTA GCTGCTCAAA  250
CATGTGCATA TATGGCTACA ACACATCCTG ATTTTTCTAT ATTAGCTGCA  300
CGTATTACTA CAGATAATTT GCACAAAAAT ACTAGTGATG ATGTTGCAGA  350
AGTAGCTGAA GCATTGTATA CGTATAAAGA TGGTAGAGGT AGACCAGCTA  400
GCTTAATTAG TAAGGAAGTA TATGATTTTA TTTTATTACA TAAAGTACGT  450
TTAAATAAAG AAATAGATTA TACTACCCAT TTTAATTATG ATTATTTTGG  500
ATTTAAAACA TTGGAAAGAT CTTATTTATT ACGTATTAAT AATAAAATTA  550
TTGAAAGACC TCAACATTTA TTAATGAGAG TTTCTATTGG TATACATATA  600
GATGACATAG ATAAAGCTTT AGAAACATAT CATTTAATGT CTCAGAAATA  650
TTTTACCCAT GCAACTCCTA CATTGTTTAA TTCAGGAACC CCAAGGCCAC  700
AAATGTCTTC TTGTTTCTTG TTATCAATGA AAGCAGATTC TATTGAAGGT  750
ATTTTTGAAA CTCTAAAACA ATGTGCTTTA ATTAGTAAAA CTGCAGGAGG  800
TATTGGTGTA GCAGTACAAG ATATAAGAGG ACAAATTCT TATATTAGAG   850
GTACCAATGG AATATCTAAT GGTTTAGTAC CTATGTTAAG AGTTTTTAAT  900
GATACTGCAA GATATGTAGA TCAAGGTGGA GGAAAACGTA AGGGATCGTA  950
CGCTGTTTAT ATTGAACCAT GGCATTCAGA TATATTTGAA TTTTTAGATT 1000
TAAGAAAGAA TCATGGAAAA GAAGAATTAA GAGCACGAGA TTTATTTTAT 1050
GCTGTATGGG TTCCTGATCT TTTTATGAAG AGAGTTAAAG AAAATAAAAA 1100
TTGGACATTA ATGTGTCCAA ATGAATGTCC AGGTTTAAGT GAAACCTGGG 1150
GTGAAGAATT TGAAAAATTA TATACAAAAT ATGAAGAAGA AAATATGGGA 1200
AAAAAAACTG TGCTTGCTCA AGATTTATGG TTTGCTATAT TACAAAGCCA 1250
AATAGAAACA GGAGTACCCA TATATCTATA TAAAGATTCT TGTAATGCAA 1300
AACCAATCAA AAATTTAGGT ACAATTAAAT GTAGTAACTT ATGTTGTGAA 1350
ATAATCGAAT ATACCTCTCC TGATGAAGTT GCTGTATGTA ATTTGGCATC 1400
TATAGCTTTA TGTAAATTTG TAGATTTGGA AAAAAAAGAA TTCAATTTCA 1450
AAAAGTTATA TGAAATAACC AAAATTATTA CAAGAAATTT AGATAAAATT 1500
ATAGAAAGAA ATTATTATCC AGTCAAAGAA GCAAAAACAT CTAATACTAG 1550
ACATAGACCT ATTGGTATTG GTGTTCAAGG ATTAGCAGAC ACATTTATGT 1600
TATTAAGATA TCTTTATGAA TCTGATGCTG CAAAAGAATT GAATAAAAGA 1650
ATATATGAAA CTATGTATTA TGCTGCTTTA GAAATGTCGG TTGATTGGCT 1700
TCAATCTGGT CCATATGAAT CTTATCAAGG AAGTCCAGGT AGCCAAGGTA 1750
TATTACAATT TGATATGTGG AATGCTAAAG TTGATAACAA ATATTGGGAT 1800
```

-continued

```
TGGGATGAAT TAAAGCTAAA GATTGCAAAA ACTGGTTTAA GAAACCTATT  1850
ATTATTAGCA CCTATGCCAA CTGCATCTAC TTCACAAATT CTTGGAAACA  1900
ATGAATCCTT TGAACCATAT ACTAGTAATA TTTATTATAG AAGAGTTTTA  1950
AGTGGAGAAT TTTTCGTTGT TAATCCTCAT TTGTTAAAAG ATTTATTTGA  2000
CAGAGGTTTA TGGGATGAAG ACATGAAACA GCAATTAATA GCTCACAATG  2050
GAAGTATTCA ATATATAAGT GAAATACCAG ATGACTTGAA AGAGTTGTAC  2100
AAAACTGTAT GGGAAATTAA GCAAAGAAT ATTATTGATA TGGCTGCAGA  2150
CAGGGGGTAT TTTATTGATC AGGTAAAATT AAAATATAAA AGATAATATA  2200
TATAAATATA AATAAATAAA TAAATAAATA AAAAAAAAA TATATATATA  2250
TATATATATA TATATATTTA TATTTATAGT GTATGTCATT TGTTTATAA   2300
GTATATATTT TGTTCATACA TTTATATTCA TATATATTTT TTTTCCTTTT  2350
TTTATAGTCC CAATCATTAA ATATTTATAT TCAAAACCA ACCTTTGCAA   2400
AATTGTCAAG TATGCATTTC TATGGATGGG AAAAAGGATT GAAAACGGGA  2450
GCTTACTATT TAAGAACCCA AGCAGCGACC GATGCTATTA AATTTACCGT  2500
CGATACTCAT GTTGCAAAAA ATGCTGTAAA ACTCAAAAAT GCAGATGGAG  2550
TACAAATAAC AAGAGAAGTT TCCAGAGAAA CAATTCAACT GAATCAACGT  2600
TACTCAAAAT GTGTGTCCTT TAAGAGTAAT AATGATGAAC AATGTTTAAT  2650
GTGTTCTGGT TAA                                         2663
```

( 2 ) INFORMATION FOR SEQ ID NO:4:

( i ) SEQUENCE CHARACTERISTICS:
        ( A ) LENGTH: 811 amino acids
        ( B ) TYPE: amino acid
        ( D ) TOPOLOGY: linear ( x i ) SEQUENCE DESCRIPTION: SEQ ID NO:4:

```
Met Tyr Val Leu Asn Arg Lys Gly Glu Glu Asp Ile Ser Phe
                  5                  10                 15
Asp Gln Ile Leu Lys Arg Ile Gln Arg Leu Ser Tyr Gly Leu His
                 20                  25                 30
Lys Leu Gly Glu Tyr Pro Ala Cys Val Thr Gln Gly Val Ile Asn
                 35                  40                 45
Gly Met Tyr Ser Ser Ile Lys Thr Cys Glu Leu Asp Glu Leu Ala
                 50                  55                 60
Ala Gln Thr Cys Ala Tyr Met Ala Thr Thr His Pro Asp Phe Ser
                 65                  70                 75
Ile Leu Ala Ala Arg Ile Thr Thr Asp Asn Leu His Lys Asn Thr
                 80                  85                 90
Ser Asp Asp Val Ala Glu Val Ala Glu Ala Leu Tyr Thr Tyr Lys
                 95                 100                105
Asp Gly Arg Gly Arg Pro Ala Ser Leu Ile Ser Lys Glu Val Tyr
                110                 115                120
Asp Phe Ile Leu Leu His Lys Val Arg Leu Asn Lys Glu Ile Asp
                125                 130                135
Tyr Thr Thr His Phe Asn Tyr Asp Tyr Phe Gly Phe Lys Thr Leu
                140                 145                150
Glu Arg Ser Tyr Leu Leu Arg Ile Asn Asn Lys Ile Ile Glu Arg
                155                 160                165
```

```
Pro Gln His Leu Leu Met Arg Val Ser Ile Gly Ile His Ile Asp
            170                 175                 180

Asp Ile Asp Lys Ala Leu Glu Thr Tyr His Leu Met Ser Gln Lys
            185                 190                 195

Tyr Phe Thr His Ala Thr Pro Thr Leu Phe Asn Ser Gly Thr Pro
            200                 205                 210

Arg Pro Gln Met Ser Ser Cys Phe Leu Leu Ser Met Lys Ala Asp
            215                 220                 225

Ser Ile Glu Gly Ile Phe Glu Thr Leu Lys Gln Cys Ala Leu Ile
            230                 235                 240

Ser Lys Thr Ala Gly Gly Ile Gly Val Ala Val Gln Asp Ile Arg
            245                 250                 255

Gly Gln Asn Ser Tyr Ile Arg Gly Thr Asn Gly Ile Ser Asn Gly
            260                 265                 270

Leu Val Pro Met Leu Arg Val Phe Asn Asp Thr Ala Arg Tyr Val
            275                 280                 285

Asp Gln Gly Gly Gly Lys Arg Lys Gly Ser Tyr Ala Val Tyr Ile
            290                 295                 300

Glu Pro Trp His Ser Asp Ile Phe Glu Phe Leu Asp Leu Arg Lys
            305                 310                 315

Asn His Gly Lys Glu Glu Leu Arg Ala Arg Asp Leu Phe Tyr Ala
            320                 325                 330

Val Trp Val Pro Asp Leu Phe Met Lys Arg Val Lys Glu Asn Lys
            335                 340                 345

Asn Trp Thr Leu Met Cys Pro Asn Glu Cys Pro Gly Leu Ser Glu
            350                 355                 360

Thr Trp Gly Glu Glu Phe Glu Lys Leu Tyr Thr Lys Tyr Glu Glu
            365                 370                 375

Glu Asn Met Gly Lys Lys Thr Val Leu Ala Gln Asp Leu Trp Phe
            380                 385                 390

Ala Ile Leu Gln Ser Gln Ile Glu Thr Gly Val Pro Ile Tyr Leu
            395                 400                 405

Tyr Lys Asp Ser Cys Asn Ala Lys Pro Ile Lys Asn Leu Gly Thr
            410                 415                 420

Ile Lys Cys Ser Asn Leu Cys Cys Glu Ile Ile Glu Tyr Thr Ser
            425                 430                 435

Pro Asp Glu Val Ala Val Cys Asn Leu Ala Ser Ile Ala Leu Cys
            440                 445                 450

Lys Phe Val Asp Leu Glu Lys Lys Glu Phe Asn Phe Lys Lys Leu
            455                 460                 465

Tyr Glu Ile Thr Lys Ile Ile Thr Arg Asn Leu Asp Lys Ile Ile
            470                 475                 480

Glu Arg Asn Tyr Tyr Pro Val Lys Glu Ala Lys Thr Ser Asn Thr
            485                 490                 495

Arg His Arg Pro Ile Gly Ile Gly Val Gln Gly Leu Ala Asp Thr
            500                 505                 510

Phe Met Leu Leu Arg Tyr Leu Tyr Glu Ser Asp Ala Ala Lys Glu
            515                 520                 525

Leu Asn Lys Arg Ile Tyr Glu Thr Met Tyr Tyr Ala Ala Leu Glu
            530                 535                 540

Met Ser Val Asp Trp Leu Gln Ser Gly Pro Tyr Glu Ser Tyr Gln
            545                 550                 555
```

-continued

```
Gly  Ser  Pro  Gly  Ser  Gln  Gly  Ile  Leu  Gln  Phe  Asp  Met  Trp  Asn
                    560                 565                      570
Ala  Lys  Val  Asp  Asn  Lys  Tyr  Trp  Asp  Trp  Asp  Glu  Leu  Lys  Leu
                    575                 580                      585
Lys  Ile  Ala  Lys  Thr  Gly  Leu  Arg  Asn  Leu  Leu  Leu  Leu  Ala  Pro
                    590                 595                      600
Met  Pro  Thr  Ala  Ser  Thr  Ser  Gln  Ile  Leu  Gly  Asn  Asn  Glu  Ser
                    605                 610                      615
Phe  Glu  Pro  Tyr  Thr  Ser  Asn  Ile  Tyr  Tyr  Arg  Arg  Val  Leu  Ser
                    620                 625                      630
Gly  Glu  Phe  Phe  Val  Val  Asn  Pro  His  Leu  Leu  Lys  Asp  Leu  Phe
                    635                 640                      645
Asp  Arg  Gly  Leu  Trp  Asp  Glu  Asp  Met  Lys  Gln  Gln  Leu  Ile  Ala
                    650                 655                      660
His  Asn  Gly  Ser  Ile  Gln  Tyr  Ile  Ser  Glu  Ile  Pro  Asp  Asp  Leu
                    665                 670                      675
Lys  Glu  Leu  Tyr  Lys  Thr  Val  Trp  Glu  Ile  Lys  Gln  Lys  Asn  Ile
                    680                 685                      690
Ile  Asp  Met  Ala  Ala  Asp  Arg  Gly  Tyr  Phe  Ile  Asp  Gln  Val  Lys
                    695                 700                      705
Leu  Lys  Tyr  Lys  Arg  Ser  Gln  Ser  Leu  Asn  Ile  Tyr  Ile  Gln  Lys
                    710                 715                      720
Pro  Thr  Phe  Ala  Lys  Leu  Ser  Ser  Met  His  Phe  Tyr  Gly  Trp  Glu
                    725                 730                      735
     Lys  Gly  Leu  Lys  Thr  Gly  Ala  Tyr  Tyr  Leu  Arg  Thr  Gln  Ala  Ala
                         740                 745                      750
Thr  Asp  Ala  Ile  Lys  Phe  Thr  Val  Asp  Thr  His  Val  Ala  Lys  Asn
                    755                 760                      765
Ala  Val  Lys  Leu  Lys  Asn  Ala  Asp  Gly  Val  Gln  Ile  Thr  Arg  Glu
                    770                 775                      780
Val  Ser  Arg  Glu  Thr  Ile  Gln  Leu  Asn  Gln  Arg  Tyr  Ser  Lys  Cys
                    785                 790                      795
Val  Ser  Phe  Lys  Ser  Asn  Asn  Asp  Glu  Gln  Cys  Leu  Met  Cys  Ser
                    800                 805                      810
Gly  811
```

( 2 ) INFORMATION FOR SEQ ID NO:5:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:5:

```
Tyr  Ala  Gly  Ala  Val  Val  Asn  Asp  Leu
                    5
```

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( D ) TOPOLOGY: linear ( x i ) SEQUENCE DESCRIPTION: SEQ ID NO:6:

```
Phe  Thr  Leu  Asp  Ala  Asp  Phe
                    5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:7:

```
    Phe  Cys  Leu  Asn  Thr  Glu  Phe
                       5
```

( 2 ) INFORMATION FOR SEQ ID NO:8:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO:8:

```
Gln  Lys  Ser  Gly  Val  Met  Ala  Gln  Arg  Lys  Asp  His  Val  Phe  Cys
                 5                        10                       15
Leu  Asn  Thr  Glu  Phe
                20
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:9:

```
  Glu  Val  Asp  Thr  Asp  Asp  Leu  Ser  Asn  Phe  Gln  Leu
                      5                        10
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:10:

```
Gly  Gly  Asn  Thr  Gly  Asp  Ser  His  Ala  Xaa  Phe  Thr  Leu  Asp  Ala
                 5                        10                       15
Asp  Phe
```

( 2 ) INFORMATION FOR SEQ ID NO:11:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:11:

```
Lys  Ser  Thr  Lys  Gln  Glu  Ala  Gly  Ala  Xaa  Phe  Thr  Phe  Asn  Glu
                 5                        10                       15
Asp  Phe
```

( 2 ) INFORMATION FOR SEQ ID NO:12:

( i ) SEQUENCE CHARACTERISTICS:
        ( A ) LENGTH: 17 amino acids
        ( B ) TYPE: amino acid
        ( D ) TOPOLOGY: linear ( x i ) SEQUENCE DESCRIPTION: SEQ ID NO:12:

Asn Ser Thr Glu Asn Ser Xaa Xaa Xaa Xaa Phe Thr Leu Asp Ala
                  5                   10                      15
Asp Phe ( 2 ) INFORMATION FOR SEQ ID NO:13:

( i ) SEQUENCE CHARACTERISTICS:
       ( A ) LENGTH: 17 amino acids
       ( B ) TYPE: amino acid
       ( D ) TOPOLOGY: linear ( x i ) SEQUENCE DESCRIPTION: SEQ ID NO:13:

Xaa Xaa Thr Glu Asn Ser Xaa Xaa Xaa Xaa Phe Thr Leu Asp Ala
                  5                   10                      15
Asp Phe ( 2 ) INFORMATION FOR SEQ ID NO:14:

( i ) SEQUENCE CHARACTERISTICS:
       ( A ) LENGTH: 17 amino acids
       ( B ) TYPE: amino acid
       ( D ) TOPOLOGY: linear ( x i ) SEQUENCE DESCRIPTION: SEQ ID NO:14:

Gln Glu Asp Asn His Xaa Xaa Xaa Xaa Xaa Phe Ser Leu Asp Val
                  5                   10                      15
Asp Phe ( 2 ) INFORMATION FOR SEQ ID NO:15:

( i ) SEQUENCE CHARACTERISTICS:
       ( A ) LENGTH: 11 amino acids
       ( B ) TYPE: amino acid
       ( D ) TOPOLOGY: linear ( x i ) SEQUENCE DESCRIPTION: SEQ ID NO:15:

Thr Ser Tyr Ala Gly Ala Val Val Asn Asp Leu
                  5                   10

( 2 ) INFORMATION FOR SEQ ID NO:16:

( i ) SEQUENCE CHARACTERISTICS:
       ( A ) LENGTH: 11 amino acids
       ( B ) TYPE: amino acid
       ( D ) TOPOLOGY: linear ( x i ) SEQUENCE DESCRIPTION: SEQ ID NO:16:

Thr Ser Tyr Ala Gly Thr Val Ile Asn Asp Leu
                  5                   10

( 2 ) INFORMATION FOR SEQ ID NO:17:

( i ) SEQUENCE CHARACTERISTICS:
       ( A ) LENGTH: 21 nucleotides
       ( B ) TYPE: nucleic acid
       ( C ) STRANDEDNESS: single
       ( D ) TOPOLOGY: linear ( x i ) SEQUENCE DESCRIPTION: SEQ ID NO:17:

GCWGAAGCWA GTTTTTGGAC A                    2 1

( 2 ) INFORMATION FOR SEQ ID NO:18:

( i ) SEQUENCE CHARACTERISTICS:
    ( A ) LENGTH: 27 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:18:

WACMCGTTTT TCAAACTTTG TTTTWCC    27

( 2 ) INFORMATION FOR SEQ ID NO:19:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:19:

ATGCTAACAC ATGCTTT    17

( 2 ) INFORMATION FOR SEQ ID NO:20:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTTTGTTTTT CCTTGAAGTG    20

( 2 ) INFORMATION FOR SEQ ID NO:21:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:21:

CTTATGTCTC AATATATAGA ATTTG    25

( 2 ) INFORMATION FOR SEQ ID NO:22:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCATCCGAAG AATTTGAAMR WYTRTAY    27

( 2 ) INFORMATION FOR SEQ ID NO:23:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:23:

ARWCCTTGWA GWCCWATWCC    20

( 2 ) INFORMATION FOR SEQ ID NO:24:

( i ) SEQUENCE CHARACTERISTICS:
  ( A ) LENGTH: 18 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:24:

TATCCAGTCA AAGAAGCA                18

( 2 ) INFORMATION FOR SEQ ID NO:25:

( i ) SEQUENCE CHARACTERISTICS:
    ( A ) LENGTH: 18 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:25:

CCATAAATCT TGAGCAAG                18

( 2 ) INFORMATION FOR SEQ ID NO:26:

( i ) SEQUENCE CHARACTERISTICS:
    ( A ) LENGTH: 7 amino acids
    ( B ) TYPE: amino acid
    ( D ) TOPOLOGY: linear ( x i ) SEQUENCE DESCRIPTION: SEQ ID NO:26:

Phe Thr Leu Asn Ala Asp Phe
                5

( 2 ) INFORMATION FOR SEQ ID NO:27:

( i ) SEQUENCE CHARACTERISTICS:
    ( A ) LENGTH: 7 amino acids
    ( B ) TYPE: amino acid
    ( D ) TOPOLOGY: linear ( x i ) SEQUENCE DESCRIPTION: SEQ ID NO:27:

Phe Cys Leu Asp Ala Asp Phe
                5

( 2 ) INFORMATION FOR SEQ ID NO:28:

( i ) SEQUENCE CHARACTERISTICS:
    ( A ) LENGTH: 7 amino acids
    ( B ) TYPE: amino acid
    ( D ) TOPOLOGY: linear ( x i ) SEQUENCE DESCRIPTION: SEQ ID NO:28:

Phe Cys Leu Asn Ala Asp Phe
                5

( 2 ) INFORMATION FOR SEQ ID NO:29:

( i ) SEQUENCE CHARACTERISTICS:
    ( A ) LENGTH: 7 amino acids
    ( B ) TYPE: amino acid
    ( D ) TOPOLOGY: linear ( x i ) SEQUENCE DESCRIPTION: SEQ ID NO:29:

Phe Thr Leu Asp Thr Asp Phe
                5

( 2 ) INFORMATION FOR SEQ ID NO:30:

( i ) SEQUENCE CHARACTERISTICS:

(A) LENGTH: 7 amino acids
(B) TYPE: amino acid
(D) TOPOLOGY: linear (xi) SEQUENCE DESCRIPTION: SEQ ID NO:30:

Phe Thr Leu Asn Thr Asp Phe
                  5

(2) INFORMATION FOR SEQ ID NO:31:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:31:

Phe Cys Leu Asp Thr Asp Phe
                  5

(2) INFORMATION FOR SEQ ID NO:32:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:32:

Phe Cys Leu Asn Thr Asp Phe
                  5

(2) INFORMATION FOR SEQ ID NO:33:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:33:

Phe Thr Leu Asp Ala Glu Phe
                  5

(2) INFORMATION FOR SEQ ID NO:34:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:34:

Phe Thr Leu Asn Ala Glu Phe
                  5

(2) INFORMATION FOR SEQ ID NO:35:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:35:

Phe Cys Leu Asp Ala Glu Phe
                  5

(2) INFORMATION FOR SEQ ID NO:36:

(i) SEQUENCE CHARACTERISTICS:
(A) LENGTH: 7 amino acids ( B ) TYPE: amino acid
( D ) TOPOLOGY: linear ( x i ) SEQUENCE DESCRIPTION: SEQ ID NO:36:

Phe Cys Leu Asn Ala Glu Phe
              5

( 2 ) INFORMATION FOR SEQ ID NO:37:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:37:

Phe Thr Leu Asp Thr Glu Phe
              5

( 2 ) INFORMATION FOR SEQ ID NO:38:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:38:

Phe Thr Leu Asn Thr Glu Phe
              5

( 2 ) INFORMATION FOR SEQ ID NO:39:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:39:

Phe Cys Leu Asp Thr Glu Phe
              5

( 2 ) INFORMATION FOR SEQ ID NO:40:

( i ) SEQUENCE CHARACTERISTICS:
        ( A ) LENGTH: 2433 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO:40:

| | | | | |
|---|---|---|---|---|
| ATGTATGTGT | TGAATAGAAA | GGGAGAAGAA | GAAGATATAT | CCTTTGATCA | 50 |
| AATTTTAAAA | AGAATACAAA | GGTTATCATA | TGGTCTTCAT | AAATTAGGTG | 100 |
| AGTATCCTGC | TTGTGTTACA | CAAGGTGTAA | TCAATGGGAT | GTATAGTAGT | 150 |
| ATAAAAACCT | GTGAATTAGA | TGAATTAGCT | GCTCAAACAT | GTGCATATAT | 200 |
| GGCTACAACA | CATCCTGATT | TTTCTATATT | AGCTGCACGT | ATTACTACAG | 250 |
| ATAATTTGCA | CAAAAATACT | AGTGATGATG | TTGCAGAAGT | AGCTGAAGCA | 300 |
| TTGTATACGT | ATAAAGATGG | TAGAGGTAGA | CCAGCTAGCT | TAATTAGTAA | 350 |
| GGAAGTATAT | GATTTATTT | TATTACATAA | AGTACGTTTA | AATAAAGAAA | 400 |
| TAGATTATAC | TACCCATTTT | AATTATGATT | ATTTTGGATT | TAAAACATTG | 450 |
| GAAAGATCTT | ATTTATTACG | TATTAATAAT | AAAATTATTG | AAAGACCTCA | 500 |
| ACATTTATTA | ATGAGAGTTT | CTATTGGTAT | ACATATAGAT | GACATAGATA | 550 |

```
AAGCTTTAGA  AACATATCAT  TTAATGTCTC  AGAAATATTT  TACCCATGCA    600
ACTCCTACAT  TGTTTAATTC  AGGAACCCCA  AGGCCACAAA  TGTCTTCTTG    650
TTTCTTGTTA  TCAATGAAAG  CAGATTCTAT  TGAAGGTATT  TTTGAAACTC    700
TAAAACAATG  TGCTTTAATT  AGTAAAACTG  CAGGAGGTAT  TGGTGTAGCA    750
GTACAAGATA  TAAGAGGACA  AAATTCTTAT  ATTAGAGGTA  CCAATGGAAT    800
ATCTAATGGT  TTAGTACCTA  TGTTAAGAGT  TTTTAATGAT  ACTGCAAGAT    850
ATGTAGATCA  AGGTGGAGGA  AAACGTAAGG  GATCGTACGC  TGTTTATATT    900
GAACCATGGC  ATTCAGATAT  ATTTGAATTT  TTAGATTTAA  GAAAGAATCA    950
TGGAAAAGAA  GAATTAAGAG  CACGAGATTT  ATTTTATGCT  GTATGGGTTC   1000
CTGATCTTTT  TATGAAGAGA  GTTAAAGAAA  ATAAAAATTG  GACATTAATG   1050
TGTCCAAATG  AATGTCCAGG  TTTAAGTGAA  ACCTGGGGTG  AAGAATTTGA   1100
AAAATTATAT  ACAAATATG   AAGAAGAAAA  TATGGGAAAA  AAACTGTGC    1150
TTGCTCAAGA  TTTATGGTTT  GCTATATTAC  AAAGCCAAAT  AGAAACAGGA   1200
GTACCCATAT  ATCTATATAA  AGATTCTTGT  AATGCAAAAC  CAATCAAAAA   1250
TTTAGGTACA  ATTAAATGTA  GTAACTTATG  TTGTGAAATA  ATCGAATATA   1300
CCTCTCCTGA  TGAAGTTGCT  GTATGTAATT  TGGCATCTAT  AGCTTTATGT   1350
AAATTTGTAG  ATTTGGAAAA  AAAAGAATTC  AATTCAAAA   AGTTATATGA   1400
AATAACCAAA  ATTATTACAA  GAAATTTAGA  TAAAATTATA  GAAAGAAATT   1450
ATTATCCAGT  CAAAGAAGCA  AAAACATCTA  ATACTAGACA  TAGACCTATT   1500
GGTATTGGTG  TTCAAGGATT  AGCAGACACA  TTTATGTTAT  TAAGATATCT   1550
TTATGAATCT  GATGCTGCAA  AAGAATTGAA  TAAAAGAATA  TATGAAACTA   1600
TGTATTATGC  TGCTTTAGAA  ATGTCGGTTG  ATTGGCTTCA  ATCTGGTCCA   1650
TATGAATCTT  ATCAAGGAAG  TCCAGGTAGC  CAAGGTATAT  TACAATTTGA   1700
TATGTGGAAT  GCTAAAGTTG  ATAACAAATA  TTGGGATTGG  GATGAATTAA   1750
AGCTAAAGAT  TGCAAAAACT  GGTTTAAGAA  ACCTATTATT  ATTAGCACCT   1800
ATGCCAACTG  CATCTACTTC  ACAAATTCTT  GGAAACAATG  AATCCTTTGA   1850
ACCATATACT  AGTAATATTT  ATTATAGAAG  AGTTTTAAGT  GGAGAATTTT   1900
TCGTTGTTAA  TCCTCATTTG  TTAAAGATT   TATTTGACAG  AGGTTTATGG   1950
GATGAAGACA  TGAAACAGCA  ATTAATAGCT  CACAATGGAA  GTATTCAATA   2000
TATAAGTGAA  ATACCAGATG  ACTTGAAAGA  GTTGTACAAA  ACTGTATGGG   2050
AAATTAAGCA  AAAGAATATT  ATTGATATGG  CTGCAGACAG  GGGGTATTTT   2100
ATTGATCAGG  TAAAATTAAA  ATATAAAAGA  TCCCAATCAT  TAAATATTTA   2150
TATTCAAAAA  CCAACCTTTG  CAAAATTGTC  AAGTATGCAT  TTCTATGGAT   2200
GGGAAAAAGG  ATTGAAAACG  GGAGCTTACT  ATTTAAGAAC  CCAAGCAGCG   2250
ACCGATGCTA  TTAAATTTAC  CGTCGATACT  CATGTTGCAA  AAAATGCTGT   2300
AAAACTCAAA  AATGCAGATG  GAGTACAAAT  AACAAGAGAA  GTTTCCAGAG   2350
AAACAATTCA  ACTGAATCAA  CGTTACTCAA  AATGTGTGTC  CTTTAAGAGT   2400
AATAATGATG  AACAATGTTT  AATGTGTTCT  GGT                      2433
```

( 2 ) INFORMATION FOR SEQ ID NO:41:

( i ) SEQUENCE CHARACTERISTICS:
  ( A ) LENGTH: 15 nucleotides
  ( B ) TYPE: nucleic acid
  ( C ) STRANDEDNESS: single
  ( D ) TOPOLOGY: linear ( x i ) SEQUENCE DESCRIPTION: SEQ ID NO:41:

ATT TTC CAT TCC AAA                                    15

( 2 ) INFORMATION FOR SEQ ID NO:42:

( i ) SEQUENCE CHARACTERISTICS:
    ( A ) LENGTH: 18 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO:42:

AAA TTC CGT ATT CAG ACA                                18

( 2 ) INFORMATION FOR SEQ ID NO:43:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:43:

Asn Ser Phe Thr Leu Asp Ala Asp Phe
                 5

( 2 ) INFORMATION FOR SEQ ID NO:44:

( i ) SEQUENCE CHARACTERISTICS:
    ( A ) LENGTH: 8 amino acids
    ( B ) TYPE: amino acid
    ( D ) TOPOLOGY: linear ( x i ) SEQUENCE DESCRIPTION: SEQ ID NO:44:

Ser Phe Thr Leu Asp Ala Asp Phe
             5

( 2 ) INFORMATION FOR SEQ ID NO:45:

( i ) SEQUENCE CHARACTERISTICS:
    ( A ) LENGTH: 6 amino acids
    ( B ) TYPE: amino acid
    ( D ) TOPOLOGY: linear ( x i ) SEQUENCE DESCRIPTION: SEQ ID NO:45:

Thr Leu Asp Ala Asp Phe
                 5

( 2 ) INFORMATION FOR SEQ ID NO:46:

( i ) SEQUENCE CHARACTERISTICS:
    ( A ) LENGTH: 5 amino acids
    ( B ) TYPE: amino acid
    ( D ) TOPOLOGY: linear ( x i ) SEQUENCE DESCRIPTION: SEQ ID NO:46:

Leu Asp Ala Asp Phe
             5

( 2 ) INFORMATION FOR SEQ ID NO:47:

( i ) SEQUENCE CHARACTERISTICS:
   ( A ) LENGTH: 7 amino acids
   ( B ) TYPE: amino acid
   ( D ) TOPOLOGY: linear ( x i ) SEQUENCE DESCRIPTION: SEQ ID NO:47:

Leu Thr Leu Asp Ala Asp Phe
                 5

( 2 ) INFORMATION FOR SEQ ID NO:48:

( i ) SEQUENCE CHARACTERISTICS:
      ( A ) LENGTH: 7 amino acids
      ( B ) TYPE: amino acid
      ( D ) TOPOLOGY: linear ( x i ) SEQUENCE DESCRIPTION: SEQ ID NO:48:

Phe Ser Leu Asp Ala Asp Phe
                 5

( 2 ) INFORMATION FOR SEQ ID NO:49:

( i ) SEQUENCE CHARACTERISTICS:
      ( A ) LENGTH: 7 amino acids
      ( B ) TYPE: amino acid
      ( D ) TOPOLOGY: linear ( x i ) SEQUENCE DESCRIPTION: SEQ ID NO:49:

Phe Ala Leu Asp Ala Asp Phe
                 5

( 2 ) INFORMATION FOR SEQ ID NO:50:

( i ) SEQUENCE CHARACTERISTICS:
      ( A ) LENGTH: 7 amino acids
      ( B ) TYPE: amino acid
      ( D ) TOPOLOGY: linear ( x i ) SEQUENCE DESCRIPTION: SEQ ID NO:50:

Phe Thr Val Asp Ala Asp Phe
                 5

( 2 ) INFORMATION FOR SEQ ID NO:51:

( i ) SEQUENCE CHARACTERISTICS:
      ( A ) LENGTH: 7 amino acids
      ( B ) TYPE: amino acid
      ( D ) TOPOLOGY: linear ( x i ) SEQUENCE DESCRIPTION: SEQ ID NO:51:

Phe Thr Phe Asp Ala Asp Phe
                 5

( 2 ) INFORMATION FOR SEQ ID NO:52:

( i ) SEQUENCE CHARACTERISTICS:
      ( A ) LENGTH: 7 amino acids
      ( B ) TYPE: amino acid
      ( D ) TOPOLOGY: linear ( x i ) SEQUENCE DESCRIPTION: SEQ ID NO:52:

Phe Thr Ala Asp Ala Asp Phe
                 5

( 2 ) INFORMATION FOR SEQ ID NO:53:

( i ) SEQUENCE CHARACTERISTICS:

(A) LENGTH: 7 amino acids
(B) TYPE: amino acid
(D) TOPOLOGY: linear (xi) SEQUENCE DESCRIPTION: SEQ ID NO:53:

Phe Thr Leu Ala Ala Asp Phe
                    5

(2) INFORMATION FOR SEQ ID NO:54:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:54:

Phe Thr Leu Asp Gly Asp Phe
                    5

(2) INFORMATION FOR SEQ ID NO:55:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:55:

Phe Thr Leu Asp Leu Asp Phe
                    5

(2) INFORMATION FOR SEQ ID NO:56:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:56:

Phe Thr Leu Asp Ala Glu Phe
                    5

(2) INFORMATION FOR SEQ ID NO:57:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:57:

Phe Thr Leu Asp Ala Asn Phe
                    5

(2) INFORMATION FOR SEQ ID NO:58:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:58:

Phe Thr Leu Asp Ala Lys Phe
                    5

(2) INFORMATION FOR SEQ ID NO:59:

(i) SEQUENCE CHARACTERISTICS:
(A) LENGTH: 7 amino acids ( B ) TYPE: amino acid
            ( D ) TOPOLOGY: linear ( x i ) SEQUENCE DESCRIPTION: SEQ ID NO:59:

Phe Thr Leu Asp Ala Ala Phe
                 5

( 2 ) INFORMATION FOR SEQ ID NO:60:

( i ) SEQUENCE CHARACTERISTICS:
            ( A ) LENGTH: 7 amino acids
            ( B ) TYPE: amino acid
            ( D ) TOPOLOGY: linear ( x i ) SEQUENCE DESCRIPTION: SEQ ID NO:60:

Phe Thr Leu Asp Ala Asp Leu
                 5

( 2 ) INFORMATION FOR SEQ ID NO:61:

( i ) SEQUENCE CHARACTERISTICS:
            ( A ) LENGTH: 6 amino acids
            ( B ) TYPE: amino acid
            ( D ) TOPOLOGY: linear ( x i ) SEQUENCE DESCRIPTION: SEQ ID NO:61:

Phe Leu Asp Ala Asp Phe
             5

( 2 ) INFORMATION FOR SEQ ID NO:62:

( i ) SEQUENCE CHARACTERISTICS:
            ( A ) LENGTH: 6 amino acids
            ( B ) TYPE: amino acid
            ( D ) TOPOLOGY: linear ( x i ) SEQUENCE DESCRIPTION: SEQ ID NO:62:

Phe Thr Leu Asp Asp Phe
             5

( 2 ) INFORMATION FOR SEQ ID NO:63:

( i ) SEQUENCE CHARACTERISTICS:
            ( A ) LENGTH: 5 amino acids
            ( B ) TYPE: amino acid
            ( D ) TOPOLOGY: linear ( x i ) SEQUENCE DESCRIPTION: SEQ ID NO:63:

Phe Thr Leu Asp Phe
             5

( 2 ) INFORMATION FOR SEQ ID NO:64:

( i ) SEQUENCE CHARACTERISTICS:
            ( A ) LENGTH: 9 amino acids
            ( B ) TYPE: amino acid
            ( D ) TOPOLOGY: linear ( x i ) SEQUENCE DESCRIPTION: SEQ ID NO:64:

Phe Thr Leu Asp Ala Asp Phe Ala Ala
                 5

( 2 ) INFORMATION FOR SEQ ID NO:65:

( i ) SEQUENCE CHARACTERISTICS:
            ( A ) LENGTH: 10 amino acids
            ( B ) TYPE: amino acid -continued (D) TOPOLOGY: linear (x i) SEQUENCE DESCRIPTION: SEQ ID NO:65:

Ala Gly Ala Phe Thr Phe Asn Glu Asp Phe
                          5

(2) INFORMATION FOR SEQ ID NO:66:

(i) SEQUENCE CHARACTERISTICS:
    (A) LENGTH: 7 amino acids
    (B) TYPE: amino acid
    (D) TOPOLOGY: linear (x i) SEQUENCE DESCRIPTION: SEQ ID NO:66:

Phe Thr Phe Asn Glu Asp Phe
                  5

(2) INFORMATION FOR SEQ ID NO:67:

(i) SEQUENCE CHARACTERISTICS:
    (A) LENGTH: 6 amino acids
    (B) TYPE: amino acid
    (D) TOPOLOGY: linear (x i) SEQUENCE DESCRIPTION: SEQ ID NO:67:

Thr Phe Asn Glu Asp Phe
              5

PLASMODIUM FALCIPARUM RIBONUCLEOTIDE REDUCTASE DNA

FIELD OF THE INVENTION

This invention relates to the ribonucleotide reductase of *Plasmodium falciparum* (Pf RR), to the subunits of Pf RR (Pf R1 and Pf R2), and to compounds comprising peptides derived from the Pf R2 C-terminus sequence that inhibit the action of protozoal RR.

BACKGROUND OF THE INVENTION

Antimalarial Therapy

Malaria is a leading cause of morbidity and mortality worldwide. It accounts for more than one million deaths annually. Malaria caused by the parasite *Plasmodium falciparum* (hereinafter "Pf"), is the most deadly of four malarial parasites.

The Anopheles mosquito-borne Pf malaria has frustrated scientists for more than a century in the worldwide quest to control malaria. The problem is compounded by emergence of drug resistant strains and slow progress in developing an effective vaccine. Thus, more effective antimalarial agents are needed.

According to the World Health Organization malaria is a major disease, that is steadily spreading today. The WHO estimates that 270 million people now carry the parasite. In 103 countries people are currently at risk from malaria. This amounts to nearly half of the world's population.

Ribonucleotide Reductase

Ribonucleotide reductase (hereinafter "RR"), is a ubiquitous biological catalyst necessary for DNA biosynthesis in all forms of life. It controls an early rate-limiting reaction in de novo DNA synthesis. This single enzyme catalyses the first step in each of the parallel pathways to the four deoxyribonucleoside triphosphates. By reducing ribonucleotides to their corresponding deoxyribonucleotides, RR provides cells with precursors needed for DNA biosynthesis and replication. Hence, viral, bacterial and eukaryotic (e.g., protozoan and mammalian) cellular proliferation inter alia is dependent upon the presence of the active enzyme. Another requirement for activity is a pool of ribonucleotide diphosphates (NDPs) and triphosphates (NTPs).

RR occurs in two subunits, $\alpha$ and $\beta$, which must be associated with each one for activity. Subunit $\alpha$ is comprised of two identical R1 subunits. Subunit $\beta$ is comprised of two identical R2 subunits. The R1 and R2 subunits generally have molecular weights of 84–90 and 37–45 kDa, respectively. Each subunit plays a critical role in the reduction process of DNA biosynthesis, and each is coded for by a distinct gene. Separation of subunit types leads to complete loss of reduction activity, which can be recovered only upon reassociation of the holoenzyme.

The fraction of fully conserved amino acid residues among all known RR sequences is low (6% in R1 and 5% in R2). Eukaryotic R2 sequences from unrelated organisms may be related for up to seven residues from the C-terminus, but the sequences are usually not conserved after the eighth amino acid residue from the C-terminus. Therefore, peptide RR inhibitors are thought to be species specific, or at least specific for related species. (Yang et al., *FEBS Lett.* 272, 61–64 (1990)).

However, R2 sequence identity may occasionally be quite high between related organisms. Homology between mouse and human forms exceeds 90%. (Pavloff et al., *J. of DNA Sequencing and Mapping* 2, 227–234 (1992)). For example, it has been demonstrated that the acylated peptide Ac-(SEQ ID NO:6), corresponding to the C-terminus of mouse R2, inhibits human RR with an $IC_{50}$ of about 10–20 µM. It is anticipated that an acylated heptapeptide corresponding to the C-terminus of human R2 would inhibit human RR with a similar $IC_{50}$.

Ordinarily, a short synthetic peptide having a sequence the same as the R2 C-terminus of a species should inhibit that species RR with an $IC_{50}$ of 10–20 µM. For example, an acetylated synthetic peptide of nine amino acid residues, identical to the herpes simplex R2 C-terminus sequence, was used to inhibit viral RR activity by competing with herpes simplex R2 for association with herpes simplex R1. The nonapeptide, Ac-(SEQ ID NO:5) had an $IC_{50}$ of 10–20 µM (Dutia et al., *Nature* 321, 439–441 (1986); Cohen et al., *Nature* 321, 441–443 (1986); Clements et al., *Virology* 162, 270–273 (1988); and Paradis et al., *J. Biol. Chem.* 263, 16045–16050 (1988)).

The Pf parasite develops in erythrocytes. Mature human erythrocytes do not have RR to produce DNA, therefore, parasitic RR function will not be replaced if the parasitic RR is deactivated. Deactivation of parasitic RR without deactivating the host enzyme in the host's non-erythrocytic cells is a feasable and particularly attractive therapeutic goal.

Pf RR has not been isolated or characterized; nor have its respective genes been isolated or sequenced. Isolation is expected to be difficult since protozoan RR activity is present in host cells only at very low levels.

SUMMARY OF THE INVENTION

The invention provides a DNA segment comprising a sequence according to SEQ ID NO:1 or SEQ ID NO:3, wherein the DNA segment consists essentially of a nucleotide sequence encoding for a polypeptide according to SEQ ID NO:2 or SEQ ID NO:4, respectively. SEQ ID NO:2 and SEQ ID NO:4 comprise the Pf R1 and Pf R2 subunits of Pf RR, respectively.

In another embodiment, the present invention provides a plasmid transfer or storage vector comprising a DNA segment consisting essentially of a nucleotide sequence encoding for a polypeptide having essentially the sequence according to amino acid SEQ ID NO:2 or SEQ ID NO:4. Such a plasmid transfer or storage vector may comprise a DNA segment having essentially the nucleotide sequence according to SEQ ID NO:1 or SEQ ID NO:3.

In another embodiment, the present invention provides a host cell transformed by a vector comprising a DNA segment consisting essentially of a nucleotide sequence according to SEQ ID NO:1 or SEQ ID NO:3. Under culture conditions the host cell is capable of producing a polypeptide having essentially the amino acid sequence according to SEQ ID NO:2 or SEQ ID NO:4.

In a further embodiment the present invention provides a method for producing a polypeptide having essentially a sequence according to SEQ ID NO:2 or SEQ ID NO:4, such method comprising the steps of:

cloning into a host cell a DNA segment encoding for a polypeptide having essentially the amino acid sequence according to SEQ ID NO:2 or SEQ ID NO:4, thereby producing a transformed host cell;

culturing the transformed host cell under such conditions as to produce the polypeptide; and isolating or purifying the polypeptide from the culture media and/or the transformed host cells.

In another embodiment, the present invention provides antimalarial compounds which are specific inhibitors of *P. falciparum* ribonucleotide reductase and which have little or no toxicity toward humans. The antimalarial compounds comprise peptides having a chain length of from seven to about 400 amino acids, preferably from seven to about 100 amino acids, and most preferably, from seven to about 20 amino acids. These compounds have the following formula:

$$Y\text{-}X_1\text{-Phe-}X_3\text{-Leu-}X_4\text{-Phe-}X_2; \quad (I)$$

wherein Y is H or a blocking group on the peptide N-terminal amino group; $X_1$ is from zero to about 393 amino acids, provided when $X_1$ is more than one amino acid, the amino acids are either the same or different; $X_2$ is OH or at least one amino acid, provided when $X_2$ is more than one amino acid, the amino acids are either the same of different; $X_3$ is any amino acid; $X_4$ is from zero to three amino acids, provided when $X_4$ is more than one amino acid, the amino acids are either the same or different; and further providing that the total amino acids of the sequence corresponding to the segment -Leu-$X_4$-Phe-$X_2$ of formula (I) is five amino acids.

Preferred compounds according to formula (I) are those wherein $X_1$ is from zero to about 93 amino acids. More preferred compounds are those compounds wherein $X_1$ is from zero to about thirteen amino acids, and Y is a blocking group on the peptide N-terminal amino group when $X_1$ is from zero to about three amino acids.

Particularly preferred compounds according to formula (I) are those compounds wherein $X_1$, $X_2$, and $X_3$ are defined as above, and $X_4$ is a group selected from the group consisting of one of the following sequences:

Xaa-Xaa-Xaa; (II)

Xaa-Xaa-Glu; (III)

Xaa-Thr-Xaa; (IV)

Asn-Xaa-Xaa; (V)

Xaa-Thr-Glu; (VI)

Asn-Xaa-Glu; (VII)

Asn-Thr-Xaa; (VIII)

and

Asn-Thr-Glu (IX);

wherein each Xaa of sequences II–VIII is the same or different and is independently any amino acid. Most preferred compounds are such compounds wherein $X_3$ is Cys. Even more preferred are compounds which comprise a sequence according to SEQ ID NO:7.

Preferred antimalarial compounds according to the present include, but are not limited to, blocked peptides derived from the Pf R2 C-terminus (SEQ ID NO:2).

In another embodiment the present invention provides unblocked intermediate peptide compounds wherein $X_1$ is from zero to about three amino acids, which are useful for preparing blocked derivatives.

In a yet further embodiment, antimalarial compositions are provided which comprise a pharmaceutically acceptable carrier and at least one compound according to the invention having a peptide length from 7 to about 20 amino acids, which inhibits Pf RR reduction of ribonucleotides to 2'-deoxyribonucleotides.

In another embodiment, the present invention provides a method of therapeutic treatment and prevention of malaria caused by *P. falciparum* by controlling the proliferation of *P. falciparum* comprising administering to a patient an effective amount of at least one antimalarial compound according to the invention having a peptide length from 7 to about 20 amino acids, such that Pf RR reduction of ribonucleotides to 2'-deoxyribonucleotides is inhibited.

In another embodiment the present invention provides a recombinant Pf RR enzyme comprising Pf R1, or a functionally equivalent polypeptide thereof and/or Pf R2, or a functional equivalent thereof. Preferably said recombinant Pf RR enzyme has the formula $(\text{Pf R2})_2$-$(\text{Pf R1})_2$ wherein said Pf R2 and Pf R1 each comprise a sequence according to SEQ ID NO:2 and SEQ ID NO:4, respectively.

In a further embodiment the present invention provides a method for screening potential antimalarial agents for antimalarial activity which comprises contacting said potential antimalarial agents with Pf RR and assaying for inhibition of Pf RR enzymatic activity.

In another embodiment the present invention provides a method for screening potential antimalarial agents for antimalarial activity which comprises contacting said potential antimalarial agents with Pf R1 and assaying for binding of said agents to Pf R1, optionally in the presence of Pf R2. In a preferred method said potential antimalarial agent is contacted with Pf R1 in the presence of Pf R2, or is contacted with Pf R1 followed by contact with Pf R2, and assayed for the blocking of Pf R1 binding to Pf R2.

The present invention further provides a method of diagnosing the presence or absence of a malarial parasitic infection in a host which comprises:

a) obtaining a blood sample from a host in need of diagnosis for the presence or absence of a malarial parasite;

b) contacting said sample with a PCR primer pair which is capable of amplifying a R1 or R2 target DNA segment of said malarial parasite, which target DNA segment is unique as compared to said host DNA, under conditions such that said primer pair will amplify said target DNA segment if said target DNA segment is present;

c) contacting said sample with a polynucleotide probe which is capable of specifically hybridizing with said target DNA segment, under conditions such that said polynucleotide probe will hybridize with said target DNA segment if said target DNA segment is present; and d) assaying said sample to determine the presence or absence of said malarial parasite.

DESCRIPTION OF THE FIGURES

FIG. 1 is a graph showing the inhibition of calf thymus/mouse ribonucleotide reductase activity by the acylated polypeptide, Ac-(SEQ ID NO:7).

DETAILED DESCRIPTION OF THE INVENTION

Unless specifically stated otherwise, all sequences are indicated as follows. All peptide sequences have their N-terminus to the left and their C-terminus to the right. All nucleotide sequences have their 5'-terminus to the left and their 3'-terminus to the right. Further, when a single dash is shown in any polypeptide sequence it indicates a single peptide covalent bond or a mimic bond bridging the two amino acid residues. The compounds according to formula I include both polypeptides comprised of ordinary amino acids and amino acid derivatives which are used to produce conformational mimics of the active polypeptide structure. The term "amino blocking group" as referred to above, or in the text and claims below, means any group capable of blocking an N-terminal amino group of a polypeptide, by replacing a hydrogen atom. For example, the blocking group may comprise an acetyl group.

Based upon the isolation of Pf R2 genomic DNA and elucidation of the corresponding amino acid sequence, compounds have been derived which are protozoan-specific. These compounds do not significantly inhibit mammalian RR enzyme. Thus, they are useful for controlling proliferation of protozoan parasites in mammals. The peptides are specific inhibitors of Pf RR and are believed to have little or no toxicity toward humans. Inhibition of Pf RR halts the malarial parasite's intraerythrocytic maturation since mature erythrocytes do not have their own RR.

The N-terminally blocked antimalarial peptides may be prepared from peptide intermediates derived from the Pf R2 C-terminus and from functionally equivalent derivative peptides. When $X_1$ is from zero to about three amino acids, the N-termini of the intermediate peptides are preferably blocked to provide better mimics of the intact native Pf R2 protein. Blocking the N-terminal amino group can lead to improved Pf R1 binding and inhibition of RR activity. Any blocking group which can be attached to an amino group either directly or through an intermediate linking group may be used. Acyl groups are preferred, of which acetyl or benzoyl groups are most preferred. Acetylating and benzoylating agents, and procedures for blocking amino terminal groups of peptides, are well known to those skilled in the art.

Isolation and Characterization of Pf RR DNA

We have found that the genes encoding Pf R1 and Pf R2 are both located on chromosome 14 of the *Plasmodium falciparum* eukaryotic protozoan. By contrast, in the mouse and human eukaryotic RR, the subunit genes are located on different chromosomes (Brissenden et al., *U. Exp. Cell. Res.* 174, 302–308, (1988); Yang-Feng et al., *U. Genomics* 1, 77–86 (1987)). Northern analysis of messenger RNA derived from synchronized cultures of Pf shows a single transcript of approximately 2100 and 5200 nucleotides per R2 and R1 respectively. The R2 transcript appears approximately 12 hours earlier, and persists approximately 12 hours longer, than the R1 transcript. This pattern of transcript accumulation is different from that seen in the mammalian (mouse) system, where levels of both R1 and R2 transcripts rise and decline in parallel as cells progress through M-phase into $G_2$+M phase (Bjorklund et al., *Biochemistry* 29, 5452–5458 (1990)).

Characterization of the R2 DNA sequence and derivation of the corresponding polypeptide sequence was carried out as follows.

Parasites were obtained and stored as described by Taraschi, et al. *Science* 232 102–104 (1986). Genomic DNA was purified essentially as described by Medrano, et al., *Biotechniques* 8, 43–45 (1990) with minor modifications to optimize yields.

Infected RBCs were collected by centrifugation, rinsed and then incubated in a lysing solution to lyse the RBCs and release the parasites. Freed parasites were rinsed and incubated with RNase and a protease to digest RNA and proteins present in the mixture. After proteins and RNA were removed, the DNA was purified and amplified with polymerase chain reaction (PCR) primers designed to amplify R2 DNA.

After amplification, the resulting DNA was made blunt-ended with a T4 polymerase, kinased with T4 polynucleotide kinase and ligated to a plasmid. The recombinant plasmids were isolated by standard techniques.

The Pf R2 N-terminal nucleotide sequence was isolated from the recombinant plasmid genomic Pf DNA by anchored PCR (APCR). The genomic Pf DNA was digested with Xba1. Fragments were selected and gel purified from agarose gel. Size-selected DNA was ligated to a plasmid and samples of the ligation mix were amplified with PCR primers. Resulting fragments were gel purified, reamplified and directly sequenced by chain termination reactions via procedures set forth in Thein, *Comments* (USB Technical Guide) 16 8 (1989).

The Pf R2 C-terminal nucleotide sequence was isolated from the recombinant plasmid genomic DNA by forced cloning and screening of colonies as follows.

Genomic DNA was digested with Ase1 and Xba1 enzymes and fragments were size-selected from agarose gel. A Nde1 site was inserted the EcoR1 site of Bluescript KS+ via Nde1-EcoR1 linkers. The digested genomic Pf DNA was ligated into KS+ digested with Xba1 and Nde1 (digested KS+ is designated Bluescript KS-NdeI). DH5α *E. coli* cells were transformed by inserting the ligation mix. Colonies were screened for positive clones by standard procedures with a fragment of R2 amplified from high molecular weight DNA with PCR primers.

The positive clones were isolated and lysed to release the plasmids, which were then digested to yield Pf DNA fragments, the resulting DNA fragments were sequenced as described above for the N-terminal segment.

The entire Pf R2 genomic DNA sequence is set forth in SEQ ID NO:1, and the amino acid sequence for Pf R2 is set forth in SEQ ID NO:2. There is no evidence of introns in Pf R2. By comparison, mouse R2 contains 10 exons and 9 introns (Thelander et al., *Embo J.* 8, 2475– 2479 (1989)).

The DNA sequence for Pf R1 was obtained substantially in the manner described above for obtaining the Pf R2 DNA sequence. The polypeptide sequence coded for by the Pf R1 DNA sequence, was then readily obtained by conventional procedures. The entire Pf R1 genomic DNA sequence is set forth in SEQ ID NO:3, and the amino acid sequence for Pf R1 is set forth in SEQ ID NO:4. In SEQ ID NO:3, nucleotides 1–63 are a non-coding 5' end; nucleotides 64–2193 code for amino acids corresponding to SEQ ID NO:4 positions 1–710; nucleotides 2194–2357 are a non-coding intron; nucleotides 2358–2660 code for amino acids corresponding to SEQ ID NO:4 positions 711–810; and nucleotides 2661–2663 are a non-coding terminating 3' end. SEQ ID NO:40 is a DNA segment coding for a polypeptide having a sequence according to SEQ ID NO:4 and corresponds to SEQ ID NO:3, with the non-coding nucleotide segments removed. The DNA segment and polypeptide according to SEQ ID NO:3 and SEQ ID NO:4, respectively, are useful as intermediates to form the recombinant Pf RR complex and as reagents to develop and test antimalarial agents.

Recombinant Production of the Pf R1 Subunit

The Pf DNA segment that codes for the Pf R1 subunit, may be cloned in a baculovirus system, essentially as described by Salem, et al., *FEBS Lett.*, 323, No. 1,2, 93–95 (1993), as follows.

A. Obtaining and Amplifying a DNA Segment Coding for the Pf R1 Subunit

The Pf R1 DNA segment, having a sequence according to SEQ ID NO:3, is first obtained from parasites that are maintained and stored as described by Taraschi, et al. *Science* 232 102–104 (1986). Genomic DNA is purified essentially as described by Medrano, et al., *Biotechniques* 8, 43–45 (1990) with the following modifications. Infected red blood cells (RBCs) from culture plates are collected by centrifugation and rinsed with phosphate buffered saline (PBS). The packed, infected RBCs are resuspended in PBS. Saponin is added followed by incubating to release the parasites.

Freed parasites are rinsed with PBS, resuspended in lysis buffer and incubated at 37° C. RNase and protease are added to the solution which is incubated to digest the RNA and protein present. The digested proteins are precipitated by adding salt to the solution. The solution is then extracted with solvent such as phenol/chloroform. DNA is precipitated with ethanol, washed and resuspended in water.

Two sets of polymerase chain reaction (PCR) primer pairs are used to amplify Pf R1 exons. The first pair is complementary to the N-terminus of SEQ ID NO:3 and a sequence adjacent to the 5' end of the intron. The second pair is complementary to a sequence adjacent to the 3' end of the intron and to the C-terminus of SEQ ID NO:3. The primer pairs are designed to amplify Pf R1 DNA exons and to add NheI restriction sites to the N-terminus and C-term-inus of the Pf R1 DNA segments. Samples of total genomic DNA, obtained from Pf as described above, are amplified via PCR with the PCR primers. Ligation of the two exons is performed by standard methods.

B. Construction of the pBlueBac2-Pf R1 Vector

The amplification product from the above amplification process is digested with NheI and inserted into the NheI site of pBlueBac2 (InVitrogen, San Diego, Calif.) to produce a Pf R1 vector (pBlueBac2-Pf R1). *Spodoptera frugiperda* (Sf9) cells (InVitrogen, San Diego, Calif.) are transformed with the recombinant plasmid using the cationic liposome method (Hartig et al., *Biotech.*, 11, 310–313 (1991). Positive clones are selected by beta-galactosidase blue/white screening and subsequently grown in culture dishes. Plaques are subjected to PCR analysis with primers complementary to the polyhedron loci to select those free of non-recombinant baculovirus.

C. Growth and Maintenance of Sf9 Cells

Sf9 cells are cultured in Excell 400 medium (JRH Scientific, Lenexa, Kans.) supplemented with heat inactivated fetal calf serum (FCS) (Bethesda Research Labs, Gaithersburg, Md.) gentamycin and Fungizone that has been sterile filtered. Cells grown in spinner flasks are also sup-plemented with 0.1% Pluronic F-68 (JHR Scientific, Lenexa, Kans.) to reduce shear damage.

D. Expression of Recombinant Pf R1

Original stocks of recombinant virus, produced as above, are used to infect virgin Sf9 cells to screen for protein production and generate the second generation of virus. Aliquots of the infected Sf9 cells are removed and assayed intermittently for expression of recombinant Pf R1 protein. Plaques producing Pf R1 protein without viral contamination of the protein are selected for further study. Larger culture volumes are grown and harvested by centrifugation to produce a cell pellet.

E. Purification of Recombinant Pf R1

The cell pellet collected from the culture is resuspended in lysis buffer and subjected to cycles of freeze-thaw. The lysate is centrifuged to produce a supernatant which is loaded directly onto a Sepharose affinity column (to which a short peptide corresponding to Pf R2 C-terminus is bound) using the method described in Yang, et al., *FEBS Lett.* 272 61–64 (1990)). The column is washed with a buffer and then with a small volume of buffer+KCl to elute the recombinant Pf R1. The column is regenerated by treatment with 6M guanidine-HCl. Column fractions are monitored by the Bradford assay (Bradford, Id. (1976)).

F. Recombinant Pf R1 Identification

A partial N-terminal sequence of the purified protein is determined by the Edman method (Edman, et al. *Eur. J. Biochem.* 1 80–91 (1967) using an Applied Biosystems model 473A sequencer. SDS polyacrylamide gel electrophoresis (SDS-PAGE) is performed using 7.5% acrylamide. Western blots are performed as described in Rubin et al. *J. Biol. Chem.* 265, 1199–1207 (1990) using a polyclonal antibody raised against a synthetic protein segment of Pf R1 which is unique to Pf R1 as obtained from SEQ ID NO:3. Protein concentration is determined according to the Bradford assay (Bradford, *Anal. Biochem.* 72 248–254 (1976).

Recombinant Production of the Pf R2 Subunit

Expression of recombinant Pf R2 is based on transcription of T7 RNA polymerase according to the method of Mann, et al., *Biochem.* 30 1939–1947 (1991)). The Pf R2 protein is expressed and purified to homogeneity following a rapid and simple purification procedure. The Pf R2 protein is expressed from T7 RNA polymerase responsive plasmids, which are constructed by using standard molecular cloning techniques. Plasmids are propagated in *E. coli* strains grown in LB medium at 37° C., in the presence of carbenicillin. Transfections are performed by using the procedure according to Hanahan (*J. Mol. Biol.* 166 557–580 (1983)).

A. Obtaining and Amplifying a DNA Segment Coding for the Pf R2 Subunit

The Pf R2 DNA segment, having a sequence according to SEQ ID NO:1, and coding for Pf R2, is first obtained from parasites in the same manner as the Pf R1 segment is obtained above.

A polymerase chain reaction (PCR) primer pair terminated with a NheI restriction site, for example, and complementary to the N-terminus and C-terminus of SEQ ID NO:1, respectively, is designed. The primers amplify Pf R2 DNA and add a NheI restriction site to the N-terminus and to the C-terminus of the Pf R2 DNA segments. The Pf R2 DNA segment is amplified by PCR in the same manner as for Pf R1, above.

B. Construction of the pET3a-Pf R2 Vector

The Pf R2 PCR amplification product is cleaved with NheI restriction enzyme to produce a NheI Pf R2 DNA fragment construct. This Pf R2 construct is transferred into the T7 expression vector pET3a (Rosenberg et al., *Gene* 56 125–135 (1987); Studier et al., *Methods Enzymol.*, 185 60–89 (1990)) opened with the same enzyme. The resulting pET3a-Pf R2 vector is transfected into an *E. coli* strain which contains a lac(IPTG)-inducible, chromosomal copy of the T7 RNA polymerase gene. The plasmid pET3a and the bacterial strain BL21(DE3), are described in Studier, et al., *Methods Enzymol.*, 185 60–89 (1990).

C. Growth and Maintenance of *E. coli* Cells

Typically, BL21 (DE3) *E. coli* bacteria transfected with the pET3a-Pf R2 plasmid are logarithmically grown in LB medium containing carbenicillin. The LB medium is infected with a small quantity of overnight cultures of BL21(DES) bacteria, which is then cultured under agitation at 37° C. The LB medium containing the BL21(DES) bacterial culture is supplemented with IPTG when the absorption density is at $A_{590}$ is 0.6–1.0. The BL21(DE3) bacteria may then be cultured for a few additional hours before harvesting.

D. Expression of Recombinant Pf R2 Protein

Pf R2 protein is produced by induction of logarithmically growing BL21(DE3) bacteria containing plasmid pET3a-Pf R2 as described above. After incubation as described above, the cultures are chilled and centrifuged to produce a pellet. The pellet from the first centrifugation is gently resuspended in a buffer and again centri-fuged. The pellet from the second centrifugation is fro-zen in liquid nitrogen and stored frozen until recombi-nant Pf R2 is to be purified from the pellet.

E. Purification of Recombinant Pf R2 Protein

Each purification protocol involves disintegration of frozen bacteria containing the Pf R2 protein, extraction into a buffer, precipitation of nucleic acids with streptomycin sulfate, ammonium sulfate precipitation, and anion-exchange chromatography. All operations are performed in a cold room.

Pf R2 preparation, which is a modification of the previously published procedure for preparing recombinant *E. coli* R2 (Sjöberg et al., *Biochem.* 261 5658–5662 (1986)), is described in detail where it differs from the published method.

Protein concentrations and purity may be assessed by Coomassie Brilliant Blue dye binding, with reference to a bovine serum albumin standard (Bradford, et al., *Anal. Biochem.*, 72 148–254 (1976)), combined with laser densitometric (LKB Pharmacia, Piscataway, N.J.) scanning of TCA-precipitated samples separated on 10% SDS-polyacrylamide gels (Engström et al., *Biochem.*, 18 2941–2948 (1979)). Concentrations of highly purified proteins are measured by light absorbance and calculated from extinction coefficients, as discussed below.

Frozen pellets of *E. coli* bacteria containing plasmid pET3a-Pf R2 are obtained from the above cultures and centrifugation. The pellets are finely ground in a mortar with cold aluminum oxide (Sigma Chemical Co., St. Louis, Mo.), using liquid nitrogen as necessary to prevent thawing. The powder is either stored frozen or directly mixed and thawed rapidly on ice in extraction buffer and centrifuged. Streptomycin sulfate is added to the supernatant to a final concentration of 2.5% while stirring on ice, followed by centrifugation. Solid ammonium sulfate is then added to the supernatant and the precipitate is recovered by centrifugation. After the precipitate is dissolved in extraction buffer, the extract is iron-reactivated (see below) or directly equilibrated (apo-Pf R2 preparations) in a buffer on a column containing Sephadex G-25 medium. Then about 30 mg of partially purified Pf R2 is loaded onto a DEAE-cellulose column (DE 52, Whatman Laboratory Products, Inc., Clifton, N.J.), previously equilibrated with 10 mM potassium phosphate, pH 7.0, 30 mM KCl, and 1 mM EDTA. The column is washed with the same buffer and Pf R2 is then eluted in 3–4 column volume of 10 mM potassium phosphate, pH 7.0, 70 mM KCl, and 1 mM EDTA. The protein eluate is frozen directly or is recovered by overnight dialysis at a low temperature against saturated ammonium sulfate. The eluted or dialysized protein is centrifuged, dissolved in Tris-HCl, pH 7.6, and is then stored frozen in aliquots.

Enzyme Activity of Recombinant Pf R1 and R2 Preparations

A. Recombinant Pf RR Activity Assay

Ribonucleotide reductase activity is assayed at 37° C. using the method of Moore and Peterson, *Biochem.* 13 2904–2907 (1974) with minor modifications. Briefly, assay mixtures contain 60 mM HEPES, pH 7.6, 26 mM DTT, 7 mM NaF, 5 mM $Mg(OAc)_2$, 3 mM ATP, 0.05 mM $FeCl_3$, and either 10 μg of recombinant Pf R2, which is prepared using the published R2 recombinant method of Mann et al. *Biochem.* 30 1939–1947 (1991), or an equivalent volume of a buffer. For CDP reductase assays, 0.05 mM [5-$^3$H]-CDP (20 Ci/mol) is added to the assay mixture, while for GDP reductase assays 1.5 mM dTTP and 0.02 mM [2,8-$^3$H]-GDP (45 Ci/mol) is added to a final volume of 100 μl. Reactions are initiated by the addition of recombinant R1 protein, and the assay mixture is incubated at 37° C. for about 5–15 minutes for initial rate deter-minations. Reactions are quenched by immersion in a boiling water bath for 4 minutes. Samples are frozen and lyophilized to dryness. Lyophilized samples are reconstituted in a buffer at a basic pH containing Tris and $Mg(OAc)_2$. Samples are centrifuged at high speed to precipitate denatured protein. The supernatant is then loaded onto columns of aminophenylboronate which had been pre-equilibrated with the same buffer. Deoxyribonucleoside diphosphates (dCDP or dGDP) are then eluted prior to the unreacted ribonucleoside diphosphate substrate and resolved from the substrate. Unreacted ribonucleoside diphosphate substrates can be quantitatively recovered and columns can be regenerated by treatment with sodium citrate, at pH 5.9. Radioactivity in aliquots of both the buffer B and citrate fractions can be determined by liquid scintillation counting.

B. Recombinant Pf R2 Activity Assay

Pf R2 is reactivated by iron and tyrosyl radial regeneration using the procedures described by Mann, et al., *Biochem.* 30 1939–1947 (1991)). After reactivation, ribonucleotide reductase/Pf R2 activity is determined from the rate of reduction of [$^3$H]-CDP. One unit is defined as the amount of protein which, in the presence of excess the Pf R1 subunit, catalyzes the formation of 1 nmol of dCDP/minute at 37° C. (Engström et al., *Biochem.*, 18 2941–2948 (1979); Ingemarson et al., *J. Virol.* 63 3769–3776 (1989)). The reactivated Pf R2 protein is assayed in the presence of 15 μg of pure Pf R1 protein, obtained as described above.

Chromosomal Location of *Plasmodium falciparum*

Chromosomal sized DNA from Pf was isolated from agarose gel blocks, which had been subjected to electrophoresis. Gels were run on a CHEF apparatus photographed and transferred to a solid support, e.g., ZetaProbe™ (BioRad Laboratories, Richmond, Calif.) following the manufacturers recommended procedures to obtain a blot. Radioisotope-labelled probes complementary to Pf R1 and R2 DNA were designed to probe the blots for Pf R1 and R2 DNA. A radioisotope-labelled chromosome 14 control probe complementary to the DNA of a gene known to be on chromosome 14 was used as a control. A Pf chromosomal-sized DNA blot hybridized to all three of the probes, i.e., R1, R2, and GPI probes. Thus, the chromosome 14 control probe verifies that genes coding for R1 and R2 are on chromosome 14.

Synthesis and Purification of Antimalarial Compounds

Peptide intermediate portions of antimalarial compounds according to the present invention may be synthesized and purified by standard methods as outlined below. The peptide intermediates may be synthesized in vitro by chemical coupling and end-product purification methods well known to the ordinary practitioner in this art. (Climent, et al., *Biochem* 30 5164–5171 (1991); and Bushweller et al., *Biochem* 30 8144–8151 (1991)). Peptides according to the invention may be prepared using conventional solid phase synthesis procedures, such as those described by Merrifield, *J. Am. Chem. Soc.* 85:2149 (1964). Other equivalent chemical syntheses known in the art can also be used, such as the synthesis of Houghten, *Proc. Natl. Acad. Sci.* 82:5132 (1985).

Other examples of acceptable peptide synthesis techniques may be found in M. Bodanszky et al., *Peptide Synthesis*, John Wiley & Sons, 2d Ed. (1976). Other peptide synthesis procedures are well-known to those skilled in the art. A summary of peptide synthesis techniques may be found in J. Stuart and J. D. Young, *Solid Phase Peptide Synthesis*, Pierce Chemical Company, Rockford, Ill. (1984). The synthesis of peptides by solutions methods may also be used, as described in *The Proteins*, vol. II, 3rd. Ed., Neurath, H. et al., Eds., p. 105–237, Academic Press, New York, N.Y. (1976). Appropriate protective groups for use in such syntheses can be found in the above texts or in J. F. W. McOmie, *Protective Groups in Organic Chemistry*, Plenum Press, New York, N.Y. (1973).

In general, these synthetic methods involve the sequential addition of one or more amino acid residues or suitably protected amino acid residues to a growing peptide chain. Normally, the amino group and, if relevant, the side chain, of each amino acid residue is protected by a suitable, selectively-removable protecting group. A different, selectively removable protecting group is utilized for amino acids containing a reactive side group, such as lysine.

In particular, polypeptides according to the present invention may be prepared to about 99% purity from (Fmoc)-amino acids on a Milligen 9600 synthesizer by automated solid-phase methods (Chang et al., *Int. J. Peptide Protein Res.* 11 246–249 (1978); Meienhofer et al., *Int. J. Peptide Protein Res.* 13 35–42 (1979)). Peptide coupling is obtained via diisopropyl carbodiimide/hydroxybenzotriazole chemistry in a solvent such as dimethyl-formamide (DMF). Fmoc groups are cleaved in a solvent such as piperidine/toluene/DMF. After removal of the final Fmoc group, the peptide is acylated. Deprotection of amino acid side chains and cleavage of the peptide from the resin is performed in trifluoroacetic acid/dimethylsulfide. The peptide can then be purified by liquid chromatography.

It is contemplated that, based upon the carboxy terminal amino acid sequence of Pf R2, peptide analogs or mimics may be prepared, blocked, and effectively screened for their ability to selectively inhibit Pf RR according to assays described later herein. It is particularly contemplated that conservative amino acid changes may be made which do not alter the biological function of the polypeptide derivative. When conservative substitutions destroy the biological function of a peptide, this can be detected by screening the peptide for its ability to selectively inhibit Pf RR. Examples of conservative changes include for instance, substituting one polar amino acid, such as threonine, for another polar amino acid such as serine; substituting one acidic amino acid, such as aspartic acid for another acidic amino acid, such as glutamic acid; substituting a basic amino acid, such as lysine, arginine or histidine for another basic amino acid; or substituting a non-polar amino acid, such as alanine, leucine or isoleucine for another non-polar amino acid.

Crude peptides may be injected into an analytical HPLC column to optimize the purification. Following elution, a sample load of 20 mg per injection may be chromatographed on a semi-preparative $C_{18}$ column such as a Dychrom 1 cm×25 cm HPLC column using a binary solvent system such as 0.1% trifluoroacetic acid (TFA) and 0.1% TFA in acetonitrile, and appropriate gradients. Peptide elution may be monitored at 214 nM. HPLC fractions may be collected, lyophilized and analyzed by mass spectrometry using fast atomic bombardment (FAB) conditions on instruments such as VG ZAB E.

The amino-blocked peptides of the invention are prepared from polypeptide intermnediates according to the peptide N-terminal blocking method previously described by Yang et al., *FEBS Lett.* 272 61–64 (1990), for example.

Antimalarial Pharmaceutical Compositions

Antimalarial compositions are provided which comprise a pharmaceutically acceptable carrier and at least one compound according to the invention which has a length of from 7 to about 20 amino acids which inhibits *P. falciparum* ribonucleotide reductase catalyzed reduction of ribonucleotides to 2'-deoxyribonucleo-tides.

The antimalarial peptide derivatives may be combined with any pharmaceutically acceptable carrier suitable for parenteral, preferably intravenous administration. Thus, the antimalarial compounds may be formulated according to conventional methods for preparing peptide agents or blocked peptide agents for parenteral administration. The optimum concentration of the antimalarial blocked peptides in the chosen medium can be determined empirically, according to procedures well known to medicinal chemists. As used herein, "pharmaceutically acceptable carrier" includes any and all solvents, dispersion media, and other ingredients which may be appropriate for the desired route of administration of the pharmaceutical peptide preparation. The use of such media for pharmaceutically active substances is known in the art. Any conventional media or agent is contemplated for use in the pharmaceutical preparation according to the invention insofar as it is compatible with the antimalarial peptides according to the invention.

The intravenous carrier most advantageously comprises a pharmaceutically acceptable buffer solution such as phosphate buffered saline at physiological pH, preferably in combination with a pharmaceutically acceptable compound for adjusting isotonic pressure, such as mannitol or sorbitol and similar substances.

The antimalarial composition may be tested for its ability to inhibit Pf RR reduction of ribonucleotides to 2'-deoxyribonucleotides via a Pf RR activity assay. The antimalarial composition is added to a recombinant Pf RR enzyme solution containing labelled ribonucleotides. For comparison a control solution is run under the same conditions, but without the anti-malarial composition being present. Both solutions are incubated, followed by assaying to determine the amount of ribonucleotides that remain. Less ribonucleotides remaining in the control solution indicates that the antimalarial composition will inhibit the Pf RR enzyme activity.

Method for Treating Malaria

Compounds according to the present invention having a length of from 7 to about 20 amino acids may be administered by any convenient route which will result in the delivery to the bloodstream of an antimalarial effective amount thereof. Contemplated routes of administration include both parenteral and oral routes. Intravenous administration is presently contemplated as the preferred administration route.

Generally, a peptide whose N-terminus is optionally blocked may be administered in an amount sufficient to obtain the desired therapeutic effect. The compounds of the invention may be administered at appropriate intervals, until the danger or symptoms of the disease are no longer evident, after which the dosage may be reduced to a maintenance level or discontinued.

As used herein, the term "patient" includes both humans and animals. The inhibition of growth and replication of the malarial organisms in red blood cells (erythrocytes) is monitored at intervals after administration to evaluate the peptide potency and clearance rates. The blood samples are also evaluated for growth and reproduction of malarial organisms, e.g., by isolation and measurement of the malarial organism's mRNA or by probing for the presence of either a Pf R1 or a Pf R2 protein with a monoclonal antibody.

After evaluation, the compound dosage may be adjusted as necessary to obtain or maintain inhibited growth and replication of malarial organisms. In the weeks that follow, the patient is again monitored once or twice weekly, until the patient is free of disease symptoms. Ordinarily, the patient is treated until all red blood cells examined are free of malarial organisms. Thus, the patient should be treated until the red blood cells containing malarial organisms die and new cells develop which are free of malarial organisms. In areas with a high risk of malarial infection, indefinite daily administration of a therapeutic dosage may be necessary to avoid an initial infection or prevent a reinfection.

Method for Detecting a Malarial Parasite in a Patient

The presence of the malarial parasite in the patient's blood can be detected by a diagnostic polymerase chain reaction (PCR) assay. In principle any two regions of parasite DNA that show sequence divergence from the host can be used for diagnostic PCR. For example, one primer can be synthesized to have a nucleotide sequence corresponding to the region of DNA coding for Pf R2 amino acid numbers 273–278. The other primer will be complementary to a nucleotide sequence coding for the Pf R2 C-terminal region (see SEQ ID NO:2). Examples of P. falciparum primers are 5'-ATT TTC CAT TCC AAA-3' (SEQ ID NO:41) and 5'-AAA TTC CGT ATT CAG ACA-3' (SEQ ID NO:42), which are upstream primer and downstream primer, respectively. Diagnostic PCR can be carried out by isolation of DNA from blood samples obtained via peripheral circulation using a variety of published methods, one of which is described below. PCR can be carried out using 1 µM of each primer above in standard PCR buffer. The above example of PCR primer pairs would amplify a fragment of Pf DNA 196 base pairs in length.

A sample containing red blood cells is obtained from a patient suspected of being infected with malarial parasites. The red blood cells are collected by centrifugation and rinsed with phosphate buffered saline (PBS) until about 6 milliliters of RBCs are obtained. The RBCs are resuspended in PBS. Saponin is added followed by incubating to release the suspected parasites. The samples suspected of having parasites are rinsed with PBS, resuspended in lysis buffer and incubated at room temperature. The solution is adjusted with RNase and protease incubated at 37° C. to digest the RNA and protein present. Digested proteins are precipitated by addition of a salt such as NaCl. The DNA is then extracted with a phenol/chloroform solvent, precipitated with ethanol, washed and resuspended in water.

A diagnostic polymerase chain reaction (PCR) assay is performed on the resuspended DNA. Primers complementary to any two regions of parasitic DNA corresponding to a portion of either SEQ ID NO:1 or SEQ ID NO:3 that showed divergence from the hosts R1 and R2 can be used for the diagnostic PCR. Analysis can be performed on approximately 10% of the sample by running the sample portion on 8.0% polyacrylamide. The primers should amplify a fragment of DNA about 196 nucleotides in length. Gels can be photographed and transferred to a solid support, e.g., ZetaProbe™ (BioRad Laboratories, Richmond, Calif.), following the manufacturer's recommended procedures to obtain a blot.

Radioisotope-labelled probes complementary to the amplified portion of the PF R1 or R2 DNA can be designed to probe the blots for the parasitic DNA. Probe binding would indicate the presence of parasitic DNA. A blood sample known to be infected by the parasite can be utilized as a control and run through the same procedures as described above to verify the diagnosis.

Antimalarial Peptides and Polypeptide Segments of Pf R1

The antimalarial polypeptides according to the invention are described as follows.

Attachment of a peptide to an Pf R1 polypeptide at the Pf R1/R2 binding site inhibits the formation of an active Pf R1/R2 complex. Pf R2-derived peptides according to the present invention display much greater binding affinity toward Pf R1 than toward a mammalian R1 enzyme. For example, the blocked peptide of Example 4 below has an $IC_{50}$ of 160 μM for binding mammalian R1. Because the present peptides preferentially bind Pf R1, substantially all the available Pf R1 can be bound by peptides, while leaving the mammalian host R1 free for association with host R2 and formation of the active host RR holoenzyme. This therapeutic effect is obtained by starting at an effective amount of a short antimalarial peptide based upon the in vitro Pf RR inhibition assay and adjusting the dosage (if necessary) until inhibition of the formation of the Pf RR holoenzyme is observed.

Thus, the blocked peptides according to the present invention, are selective inhibitors of Pf RR and are therapeutically useful antimalarial agents and may be selective inhibitors of other related protozoan RRs. Eucaryotic R2 polypeptides previously characterized have been highly homologous and have demonstrated considerable cross-reactivity with RRs of other eucaryotic species. For example, the twenty C-terminal residues of mouse and human R2 differ by only 10% (2/20). The homology is even closer for the seven C-terminal residues. The human R2 seven C-terminal amino acids are identical to those of other eucaryotic organisms such as clam and mouse.

Although Pf is a eukaryote, Pf R2 is less homologous with mammalian R2. The amino acid sequence of the Pf R2 subunit is 65% different (13/20 different amino acid positions) from mouse R2 in the twenty C-terminal residues. Moreover, the amino acid sequence of the Pf R2 subunit is 43% different from the human R2 in the seven C-terminal positions, with only three of the seven (3/7) human amino acid positions being identical to Pf R2. The conserved amino acids are underlined.

(SEQ ID NO:6) Phe-Thr-Leu-Asp-Ala-Asp-Phe (Human, Mouse and Clam), and (SEQ ID NO:7) Phe-Cys-Leu-Asn-Thr-Glu-Phe (*P. falciparum*).

Table 1, below, lists for comparative purposes C-terminal amino acid R2 sequences for various organisms.

TABLE 1

| C-TERMINAL SEQUENCES FOR R2 | |
|---|---|
| ORGANISM | SEQUENCE |
| *E. coli* | SEQ ID NO:9 |
| | EVDTDDLSNF QL |
| Clam | SEQ ID NO:10 |
| | GGNTGDSHA. FTLDADF |
| Yeast | SEQ ID NO:11 |
| | KSTKQEAGA. FTFNEDF |
| Mouse | SEQ ID NO:12 |
| [001b] | NSTENS.... FTLDADF |
| Human | SEQ ID NO:13 |
| | ..TENS.... FTLDADF |
| Vaccinia | SEQ ID NO:14 |
| | QEDNH..... FSLDVDF |
| Herpes | SEQ ID NO:15 |
| | TSYAGAVVND L |
| Varicella | SEQ ID NO:16 |
| | TSYAGTVIND L |

The practice of the invention is illustrated by the following non-limiting examples.

EXAMPLE 1

Isolation of DNA from *Plasmodium falciparum*

Parasites were maintained and stored as described by Taraschi, et al., Science 232 102–104 (1986). Genomic DNA was purified essentially as described by Medrano, et al., Biotechniques 8, 43–45 (1990) with the following modifications. Infected red blood cells (RBCs) from 10 plates were collected by centrifugation (room temperature, 9 minutes) and rinsed with phosphate buffered saline (PBS). The packed, infected RBCs (6 ml) were re-suspended in 30 ml of PBS. Saponin was added until a concentration of 0.1% was obtained, followed by incubating for 5 minutes to release the parasites.

Freed parasites were rinsed with 30 ml PBS, resuspended in 15 ml lysis buffer (2.5 mM Tris.HCl at pH 8.0, 5 mM EDTA, 4% sodium lauryl sarcosinate (Sarkosyl™)) and incubated for 5 minutes at room temperature. The solution was adjusted to 50 µg/ml RNase and 100 µg/ml of a subtilisin-type protease (e.g., Proteinase K) and incubated at 37° C. for 2 hours. Proteins were precipitated by the addition of 5 ml of 5M NaCl at 4° C. for 12 hours. The solution was then extracted with an equal volume of phenol/chloroform. The DNA was precipitated with ethanol, washed and re-suspended in water overnight at 37° C.

Polymerase chain reaction (PCR) primers were designed to amplify R1 and R2 DNA. Samples containing 1 µg of total genomic DNA obtained from Pf as described above, were amplified via PCR with 2 µM of S.N2 (SEQ ID NO:17) and S.C2 (SEQ ID NO:18) primers. The PCR procedure was performed in a 100 µl volume containing 50 mM KCl, 10 mM Tris.HCl pH=8.0, 2 mM MgCl$_2$, 2 mM each dNTP and 2.5 units Taq DNA polymerase (e.g., Amplitaq™, Perkin-Elmer, Norwalk, Conn.). Samples were subjected to 35 cycles of PCR, performed on an Ericomp thermal cycler. Each cycle was 94° C., 30 seconds; 40° C., 60 seconds; and 72° C., 90 seconds. After amplification, the DNA was made blunt-ended with T4 polymerase, kinased with T4 polynucleotide kinase and ligated to Eco RV-digested KS (+) plasmid (Stratagene, La Jolla, Calif.). The recombinant plasmids were isolated by standard techniques and sequences determined by the chain termination reaction with a modified T7 bacteriophage DNA polymerase (e.g., Sequenase™ (United States Biochemical Corporation, (USB))).

The Pf R2 N-terminal nucleotide sequence was isolated by anchored PCR (APCR). This genomic DNA was digested with Xba1. Fragments of 600–850 base pairs (bps) in length were gel purified from a 1% agarose gel. seventy nanograms of size-selected DNA from the agarose gel was ligated to 240 ng of XbaI, 4-chloro-3-indolyl phosphate (CIP) treated KS+ in a 100 µl reaction volume. Seven µl samples of the ligation mix were amplified with S.C5 (SEQ ID NO:19) and either the universal forward or reverse primers. PCR conditions were 94° C., 15 seconds; 35° C., 30 seconds; and 72° C, 90 seconds. The resulting DNA fragment was gel purified, re-amplified and directly sequenced via the procedures set forth in Thein, *Comments* (USB Technical Guide) 16 8 (1989).

The Pf R2 C-terminal nucleotide sequence was isolated by forced cloning and screening of colonies. Genomic DNA (obtained as described above) was digested with Ase1 and Xba1 enzymes. Fragments of 750–900 bps length were size-selected from a 0.7% agarose gel. A Nde1 site was inserted in EcoR1 site of Bluescript KS+ (termed KS-NdeI) via Nde1-EcoR1 linkers. One hundred µg of the size-selected, digested DNA was ligated into 50 µg Bluescript KS-NdeI digested with Xba1 and Nde1. DH5α *E. coli* cells were transformed with the ligation mix. Colonies were screened for positive clones by standard procedures with a 140 bps fragment of R2 amplified from high molecular weight DNA with S.C8 (SEQ ID NO:20) and S.N9 (SEQ ID NO:21) primers. The positive clones were isolated and lysed to release the plasmids. The plasmids were digested to yield Pf DNA fragments. The resulting DNA fragments were sequenced in the same manner described above for the N-terminal segments.

The entire Pf R2 genomic DNA sequence is set forth as SEQ ID NO:1.

EXAMPLE 2

Isolation and Sequencing of Gene Encoding for
*Plasmodium falciparum* R1

Genomic *Plasmodium falciparum* DNA was obtained as in Example 1, above, and amplified by a PCR procedure. The PCR solution contained 1 µg of genomic DNA, and 1 µM L.N2 (SEQ ID NO:22) and L.C4 (SEQ ID NO:23) primers. The PCR procedure was performed in a 100 µl sample volume containing 50 mM KCl, 10 mM Tris.HCl pH = 8, 2 mM MgCl$_2$, 2 mM each dNTP and 2.5 units of a Taq DNA polymerase, Amplitaq™ (Perkin-Elmer, Norwalk, Conn.). Samples were subjected to 35 cycles of PCR, performed on an Ericomp thermal cycler as set forth in Example 1. Each cycle was 94° C., 30 seconds; 37° C., 60 seconds; and 72° C., 60 seconds.

Extension of the R1 clone was accomplished with a Pst1 inverted PCR reaction. One hundred μg of Pst1 digested Pf DNA was self-ligated in a 40 μl volume. The entire ligation mix was subject to PCR in a 100 μl volume with L.N3 (SEQ ID NO:24) and L.C5 (SEQ ID NO:25) primers. Amplification conditions were 15 cycles (at 94° C., 30 seconds; 40° C., 30 seconds; and 72° C., 90 seconds) followed by 20 cycles (94° C., 30 seconds; 50° C., 30 seconds; and 72° C., 90 seconds).

Segments of R1 were isolated and sequenced as set forth in Example 1. The complete DNA sequence for the R1 gene is set forth as SEQ ID NO:3. The Pf R1 polypeptide encoded by the DNA sequence according to SEQ ID NO:3 is set forth as SEQ ID NO:4.

EXAMPLE 3

Preparation and Purification of Ac-(SEQ ID NO:7)

The acylated polypeptide Ac-(SEQ ID NO:7) was prepared on a Milligen 9600 synthesizer with the Fmoc procedure of Chang, et al., *Intl. J. Pep. and Prot. Res.* 11 246–249 (1978) as described in the standard Milligen protocol. Peptide coupling was achieved via diisopropyl carbodiimide/hydroxybenzotriazole chemistry in dimethylformamide (DMF). Fmoc groups were cleaved in piperidine/toluene/DMF. After removal of the final Fmoc group, the peptide was acetylated with 5% acetic anhydride/2.5% diisopropyl ethylamine. Deprotection of amino acid side chains and cleavage of the peptide from the resin was performed in trifluoro-acetic acid/dimethylsulfide or trifluoroacetic acid/1,2-ethanedithiol.

The crude peptide was initially injected onto an analytical HPLC column to optimize the purification procedure. Then, a sample load of 10–20 mg per injection was chromatographed on a semi-preparative Dychrom 1 cm×25 cm reversed phase HPLC column using a binary solvent system, consisting of 0.1% TFA and 0.1% TFA in acetonitrile, and appropriate gradients. Peptide elution was monitored at 214 nM and 258 nM. HPLC fractions were collected, lyophilized and then analyzed by mass spectrometry using FAB conditions on a VG ZAB E instrument. A mass spectrum of purified Ac-(SEQ ID NO:7) peptide showed a dominant molecular ion of 915, corresponding to an M+H peak. $^1$HNMR (1D,2D COSY, TOCSY), mass spectra, and amino acid analysis were fully in accord with the assigned structure for this acylated heptapeptide (Tables 2 and 3, below).

TABLE 2

Random Coil $^1$H Chemical Shifts for Ac- (FCLNTEF)

| Residue | $^1$H Chemical Shift (ppm) | Protons |
| --- | --- | --- |
| Phe acetyl methyl | 1.7 | CH$_3$ |
| Leu | 0.8 | δCH$_3$ (6H) |
|  | 1.4 | βCH$_2$ |
|  | 1.6 | γCH |
| Thr | 1.0 | γCH$_3$ |
|  | 0.4 | βCH |
| Glu | 2.2 | γCH$_2$ |
|  | 1.9 | βCH$_2$ |
| Phe, Asn, Cys | 2.4–3.1 | βCH$_2$ (8H) |
| Backbone methines | 4.1–4.6 | αCH (7H) |
| Asn | 6.9–7.4 | γNH$_2$ |
| Phe aromatics | 7.1–7.3 | ring (10H) |
| Amides | 7.6–8.3 | αNH (7H) |

TABLE 3

Amino Acid Analysis of Ac- (FCLNTEF)

| Amino Acid | No. Residues Found |
| --- | --- |
| Asx | 1.05 |
| Glx | 1.01 |
| Thr | 1.00 |
| CSSC | 0.51 |
| Leu | 1.00 |
| Phe | 2.00 |

EXAMPLES 4–53

Preparation and Purification of Polypeptides

Polypeptides corresponding to SEQ ID NOS: 5, 6, 8–16, 26–39, 43–67, and N-terminally acylated derivatives were produced in the same manner as in Example 3, above.

EXAMPLE 54

Peptide Inhibition of Calf Mammalian Ribonucleotide Reductase Activity

The inhibitory effects of acylated and nonacylated polypeptides on mammalian RR enzymatic activity was assayed as described in Yang, et al., *FEBS Lett.* 272 61–64 (1990)).

Calf thymus R1 was obtained and purified as described Yang, et al., id., and recombinant mouse R2 was obtained and purified from transfected *E. coli* via an expression vector (See, e.g., Mann, et al. *Biochem.* 30, 1939–1947 (1991)). The RR activity resulting from combining these purified mammalian R1 and R2 subunits was verified as described in Yang, et al.

As a control, the purified R1 was first exposed to varying amounts of an acylated heptapeptide corresponding to the 7 amino acid C-terminal sequence of mouse and human R2 (Ac-(SEQ ID NO:6), obtained by the procedure in example 3, above. After the Ac-(SEQ ID NO:6) had sufficient time to bind with the R1, the purified recombinant mouse R2 was added to the mixture, and the mixture assayed for RR activity. An IC$_{50}$ of 10–20 μM was observed. Using the same procedure, an IC$_{50}$ of 160 μM was observed for Ac-(SEQ ID NO:7)

The inventive peptide Ac-(SEQ ID NO:7) was thus about 8–16 times less potent an inhibitor on mammalian RR activity than Ac-(SEQ ID NO:6), which has an amino acid sequence identical to the seven C-terminal residues of mouse/human R2. Accordingly, Ac-(SEQ ID NO:7) has a surprisingly lower affinity for mammalian R2 than Ac-(SEQ ID NO:6).

Table 4 below shows the inhibitory potency of other acylated and unacylated peptides as compared to SEQ ID NO:6 toward mammalian RR activity.

TABLE 4

| Peptide | IC$_{50}$[a], μM | Percent R1[b] |
| --- | --- | --- |
| 1. Ac- (NSFTLDADF) Ac- (SEQ ID NO:43) | 9–15 | 100 |
| 2. Ac- (SFTLDADF) Ac- (SEQ ID NO:44) | 8–20 | 100 |
| 3. SFTLDADF (SEQ ID NO:44) | 80 | 25 |
| 4. Ac- (FTLDADF) | 8–20 | 100 |

TABLE 4-continued

| Peptide | IC$_{50}$[a], μM | Percent RI[b] |
|---|---|---|
| Ac- (SEQ ID NO:6) | | |
| 5. FTLDADF (SEQ ID NO:6) | >400[d] | <3 |
| 6. Ac- (TLDADF) Ac- (SEQ ID NO:45) | >400 | <3 |
| 7. Ac- (LDADF) Ac- (SEQ ID NO:46) | >400 | <3 |
| 8. Ac- (LTLDADF) Ac- (SEQ ID NO:47) | >400 | <3 |
| 9. Ac- (F(4'-NH$_2$)TLDADF) Ac- (F(4'-NH$_2$) - (SEQ ID NO:45)) | 100 | 10 |
| 10. Ac- (F(4'-N$_3$)TLDADF) Ac- (F(4'-N$_3$) - (SEQ ID NO:45)) | 100 | 10 |
| 11. Ac- (FSLDADF) Ac- (SEQ ID NO:48) | 40–42 | 25 ± 1.1 |
| 12. Ac- (FALDADF) Ac- (SEQ ID NO:49) | 35–40 | 24 ± 4.1 |
| 13. Ac- (FTVDADF) Ac- (SEQ ID NO:50) | 30 | 35 |
| 14. Ac- (FTFTADF) Ac- (SEQ ID NO:51) | 48–58 | 18 ± 4.2 |
| 15. Ac- (FTADADF) Ac- (SEQ ID NO:52) | 207 | 4.9 ± 0.60 |
| 16. Ac- (FTLNADF) Ac- (SEQ ID NO:26) | 25–29 | 40 ± 2.4 |
| 17. Ac- (FTLAADF) Ac- (SEQ ID NO:53) | 286–336 | 2.9 ± 0.4 |
| 18. Ac- (FTLDGDF) Ac- (SEQ ID NO:54) | 110–230 | 9 ± 0.6 |
| 19. Ac- (FTLDLDF) Ac- (SEQ ID NO:55) | 28 | 35 |
| 20. Ac- (FTLDAEF) Ac- (SEQ ID NO:56) | 450–620 | 1.7 ± 0.15 |
| 21. Ac- (FTLDANF) Ac- (SEQ ID NO:57) | 32–38 | 23 ± 1.0 |
| 22. Ac- (FTLDALF) Ac- (SEQ ID NO:58) | 29–30 | 35 ± 5.0 |
| 23. Ac- (FTLDAAF) Ac- (SEQ ID NO:59) | 34–35 | 28 ± 1.3 |
| 24. Ac- (FTLDADL) Ac- (SEQ ID NO:60) | >400 | <3 |
| 25. Ac- (FLDADF) (6 pos. del.) Ac- (SEQ ID NO:61) | 412 | 2.5 |
| 26. Ac- (FTLDDF) (3 pos. del.) Ac- (SEQ ID NO:62) | 322 | 3 |
| 27. Ac- (FTLDF) (3 & 4 pos. del.) Ac- (SEQ ID NO:63) | 364–460 | 2.5 ± 0.18 |
| 28. Ac- (FTLDADFAA) Ac- (SEQ ID NO:64) | 500 | 2.1 |

[a]IC$_{50}$ is the concentration of peptide producing 50% inhibition of activity obtined in the absence of peptide. Values are derived from Dixon plots of 4–6 concentration points. From two to four assays were run for each point. Range of IC$_{50}$ values are for two independent determinations conducted on different days.
[b]Percent relative inhibitory potency, defined as 100 × ((IC$_{50}$ Ac-(FTLDADF)/(IC$_{50}$ peptide analog)).

EXAMPLE 55

Inhibition of Mammalian and Yeast RRs

The same RR assay was conducted as in Example 54, but substituting *S. cerevisiae* (yeast) RR. A mammalian RR assay was conducted. Table 5 below shows the comparative inhibitory potency results against yeast and mammalian RR for four acylated polypeptides having an amino acid sequence according to SEQ ID NO:65–67 and 6, respectively.

TABLE 5

| Peptide | IC$_{50}$[a], μM Yeast RR | IC$_{50}$[a], μM Mammalian RR |
|---|---|---|
| 29. Ac- (AGAFTFNEDF) Ac- (SEQ ID NO:65) | 25 | — |
| 30. Ac- (FTFNEDF) Ac- (SEQ ID NO:66) | 25 | 100 |
| 31. Ac- (TFNEDF) Ac- (SEQ ID NO:67) | 600 | 600 |
| 4. Ac- (FTLDADF) Ac- (SEQ ID NO:6) | 25 | 8–20 |

[a]IC$_{50}$ is the concentration of peptide producing 50% inhibition of activity obtined in the absence of peptide. Values are derived from Dixon plots of 4–6 concentration points. From two to four assays were run for each point. Range of IC$_{50}$ values are for two independent determinations conducted on different days.

EXAMPLE 56

Recombinant Production of the Pf R1 Subunit

The Pf DNA segment that codes for the Pf R1 subunit is cloned in baculovirus system by following cloning procedures essentially as described by Salem, et al., *FEBS*, 323, No. 1,2, 93–95 (1993), as follows.

A. Obtaining and Amplifying a DNA Segment Coding for the Pf R1 Subunit

Pf R1 DNA, having a sequence according to SEQ ID NO:3, is obtained from parasites that are maintained and stored as described by Taraschi, et al. *Science* 232 102–104 (1986). Genomic DNA is purified essentially as described by Medrano, et al., *Biotechniques* 8, 43–45 (1990) with the following modifications. Infected red blood cells (RBCs) from 10 plates are collected by centrifugation (room temperature, 9 minutes) and rinsed with phosphate buffered saline (PBS). The packed, infected RBCs (6 ml) are resuspended in 30 ml of PBS. Saponin is added until a concentration of 0.1% is obtained, followed by incubating for 5 minutes to release the parasites.

Freed parasites are rinsed with 30 ml PBS, re-suspended in 15 ml lysis buffer (2.5 mM Tris.HCl at pH 8.0, 5 mM EDTA, 4% sodium lauryl sarcosinate (Sarkosyl™)) and incubated for 5 minutes at room temperature. The solution is adjusted to 50 μg/ml RNase and 100 μg/ml of a subtilisin type protease (e.g., Proteinase K) and incubated at 37° C. for 2 hours. Proteins are precipitated by the addition of 5 ml of 5M NaCl at 4° C. for 12 hours. The DNA is then extracted with an equal volume of phenol/chloroform, is precipitated with ethanol, and is washed and resuspended in water overnight at 37° C.

Polymerase chain reaction (PCR) primer pairs complementary to the N-terminus and C-terminus, respectively, of SEQ ID NO:3 or SEQ ID NO:40, which primers terminate with the NheI restriction site, are designed to amplify Pf R1 DNA and add the NheI restriction site to each end of the Pf R1 DNA segment. Samples containing 1 μg of total genomic DNA obtained from Pf as described above (or about 0.1 μg of the synthetic Pf R1 DNA segment according to SEQ ID NO:40), are amplified via PCR with 2 μM of the PCR primers. The PCR procedure is performed in a 100 μl volume containing 50 mM KCl, 10mM Tris.HCl pH=8.0, 2 mM MgCl$_2$, 2 mM each dNTP and 2.5 units Taq DNA polymerase (e.g., Amplitaq™, Perkin-Elmer). Samples are subjected to 35 cycles of PCR, which is performed on an Ericomp thermal cycler. Each cycle is 94° C., 30 seconds; 40° C., 60 seconds; and 72° C., 90 seconds.

Alternatively, a Pf R1 DNA segment is synthesized which has a sequence according to SEQ ID NO:40. Such synthesis is performed using DNA organic chemical synthetic methods well known to one of ordinary skill in the art.

B. Construction of the pBlueBac2-Pf R1 Vector

The amplification product from the above amplification process is digested with NheI and inserted into the NheI site of pBlueBac2 (InVirtrogen) to produce a Pf R1 vector (pBlueBac2-Pf R1). *Spodoptera frugiperda* (Sf9) cells are transformed with the recombinant plasmid using the cationic liposome method (Hartig et al., *Biotech.*, 11, 310–313 (1991)). Positive clones are selected by beta-galactosidase blue/white screening and subsequently grown in 3 ml volumes in a 24-well dish. Plaques are subjected to PCR analysis with primers complementary to the polyhedron loci to select those free of non-recombinant baculovirus.

C. Growth and Maintenance of Sf9 Cells

Sf9 cells are cultured at 27° C. in Excell 400 medium (JRH Scientific) supplemented with 10% heat inactivated Fetal Calf Serum (FCS) (BRL), 540 μg/ml gentamycin and 2.5 μg/ml Fungizone that has been sterile filtered. Cells grown in spinner flasks are also supplemented with 0.1% Pluronic F-68 (JHR Scientific) to reduce shear damage.

D. Expression of Recombinant Pf R1

Original stocks of recombinant virus, produced as above, are used to infect virgin Sf9 cells to screen for protein production and generate the second generation of virus. Approximately $2\times10^6$ cells are adhered to each well of a 24-well dish in a 3 ml volume and infected with 20, 100 and 500 μl of recombinant virus. Aliquots are removed and assayed for expression of Pf R1 every 24 h for 4 days. Plaques producing Pf R1 protein without viral contamination of the protein are selected for further study. For large scale expression of the Pf R1 protein, 50 ml of cells are grown to a density of $1.3\times10^6$ cells/ml and infected with $10^8$ virus particles. Cells are grown for 60–72 hours then harvested by centrifugation at 1,000×G for 10 minutes.

E. Purification of Recombinant Pf R1

The cell pellet collected from a 50 ml culture is resuspended in 5 ml of lysis buffer (50 mM Tris-Cl, pH 7.6, 0.1 mM DTT, 2 mM PMSF) and subjected to two cycles of freeze-thaw. The lysate is centrifuged at 105,000×G for 30 minutes. The resulting supernatant is loaded directly onto an FCLNTEF-Sepharose (FCLNTEF=SEQ ID NO:7) affinity column using the method described in Yang, et al., *FEBS Lett.* 272 61–64 (1990)). The column is washed with 50 mM Tris-Cl, 0.1 mM DTT (buffer A) and then with buffer A+100 mM KCl. R1 is eluted with 10 ml buffer A+500 mM KCl. The column is regenerated by treatment with 6M guanidine-HCl. Column fractions are monitored by the Bradford assay (Bradford, *Anal. Biochem.* 72 248–254 (1976).

F. Pf R1 Identification

A partial N-terminal sequence of the purified protein is determined as in the process of Edman, et al. *Eur. J. Biochem.* 1 80–91 (1967) using an Applied Biosystems model 473A sequencer. SDS polyacrylamide gel electrophoresis (SDS-PAGE) is performed using 7.5% acrylamide. Western blots are performed as described in Rubin et al. *J. Biol. Chem.* 265, 1199–1207 (1990) using a monoclonal antibody raised against a synthetic protein segment of Pf R1 which is unique to Pf R1 as obtained from SEQ ID NO:3. Production of monoclonal antibodies (MABs) specific for regions of Pf R1 such as the Pf R2 binding site is well within the skill of the ordinary practitioner in the art. For example, MABs are raised to Pf R1 and screened to determine whether binding of Pf R2 it Pf R1 is blocked. Such a MAB would be specific for Pf R1. Protein concentration is determined according to the Bradford assay (Bradford, *Anal. Biochem.* 72 248–254 (1976) .

EXAMPLE 57

Recombinant Production of the Pf R2 Subunit

Expression of recombinant Pf R2 is based on transcription of T7 RNA polymerase according to the method of Mann, et al., *Biochem.* 30 1939–1947 (1991)). The Pf R2 protein is expressed and purified to homogeneity following a rapid and simple purification procedure. The Pf R2 protein is expressed from T7 RNA polymerase responsive plasmids, which are constructed by using standard molecular cloning techniques. Plasmids are propagated in *E. coli* strain BL21(DE 3) grown in LB medium at 37° C., in the presence of carbenicillin, 50 μg/mL. Transfections are performed according to the method of Hanahan, *J. Mol. Biol.* 166 557–580 (1983).

A. Obtaining and Amplifying a DNA Segment Coding for the Pf R2 Subunit

Total Pf DNA comprising the Pf R2 DNA segment, having a sequence according to SEQ ID NO:I, and coding for Pf R2, is first obtained from parasites in the same manner as for the Pf R1 segment in Example 56, above.

PCR primer pairs terminated with a NheI restriction site and complementary to the N-terminus and C-terminus of SEQ ID NO:1, respectively, are designed. The primers amplify the Pf R2 DNA segment having a sequence according to SEQ ID NO:1 and add NheI restriction sites to the ends of the Pf R2 DNA segment. The Pf R2 DNA segment is amplified by PCR in the same manner as for Pf R1 in Example 56, above.

B. Construction of the pET3a-Pf R2 Vector

The Pf R2 PCR amplification product is cleaved with NheI restriction enzyme to produce a NheI Pf R2 DNA fragment construct. This Pf R2 construct is transferred into the T7 expression vector pET3a (Rosenberg et al., *Gene* 56 125–135 (1987); Studier et al., *Methods Enzymol.*, 185 60–89 (1990)) which is opened with the NheI restriction enzyme. The resulting pET3a-Pf R2 vector is transfected into an *E. coli* strain BL21(DE3) (Rosenberg et al., *Gene* 56 125–135 (1987)), which strain contains a lac (IPTG)-inducible, chromosomal copy of the T7 RNA polymerase gene. The plasmid pET3a and the bacterial strain BL21(DE3), are described in Studier et al., *Methods Enzymol.*, 185 60–89 (1990)).

C. Growth and Maintenance of BL21(DES) Cells

BL21 (DE3) *E. coli* bacteria transfected with the pET3a-Pf R2 plasmid are logarithmically grown in 3 L of LB medium containing carbenicillin, 50 μg/mL. The LB medium is infected with 5 mL of overnight cultures of transfected BL21(DES) bacteria and cultured under agitation, (shaken 275 times per minute) at 37° C. The LB medium containing the transfected BL21(DES) bacterial culture is supplemented with IPTG (0.5 mM) when the absorption density at $A_{590}$ is 0.6–1.0. The transfected BL21(DE3) bacteria are then cultured for an additional four hours before harvesting.

D. Expression of Recombinant Pf R2 Protein

Pf R2 protein is produced by induction of logarithmically growing BL21(DE3) bacteria containing the plasmid pET3a-Pf R2 as described above. After incubation as described above, the cultures are chilled and centrifuged at 2500 G for 15 minutes at 2° C. The pellet from the first centrifugation is gently resuspended in 100–200 mL of 50mM Tris, pH 7.6 and 1 mM EDTA, and centrifuged at 1000 G for 10 minutes. The pellet from the second centrifugaion is frozen in liquid nitrogen and stored at −70° C.

E. Purification of Recombinant Pf R2 Protein

Each purification protocol involves disintegration of the frozen BL21(DE3) bacteria pellet containing the Pf R2 protein, extraction into a buffer, precipitation of nucleic acids with streptomycin sulfate, ammonium sulfate precipitation, and anion-exchange chromatography. All operations are performed in a cold room at about +4° C.

Pf R2 preparation, which is a modification of the previously published procedure for purification and activation of recombinant E. coli R2 (Sjöberg et al., Biochem. 261 5658–5662 (1986)), is described in detail where it will differ. Protein concentrations and purity may be assessed by Coomassie Brilliant Blue dye binding, with reference to a bovine serum albumin standard (Bradford, et al., Anal. Biochem., 72 148–254 (1976)), combined with laser densitometric (LKB Pharmacia) scanning of TCA-precipitated samples separated on 10% SDS-polyacrylamide gels (Engström et al., Biochem., 18 2941–2948 (1979)). Concentrations of highly purified proteins are measured by light absorbance and calculated from extinction coefficients, as discussed below.

Frozen bacterial pellets (W g) of BL21(DE3) E. coli bacteria containing plasmid pET3a-Pf R2 are obtained from centrifugation of the above cultures. The pellets are finely ground in a mortar with 2×W g of cold aluminum oxide (Sigma), using liquid nitrogen as necessary to prevent thawing. The powder is either stored (−70° C.) or directly mixed and thawed rapidly on ice in 4×W mL of extraction buffer (50 mM Tris-HCl, pH 7.6, 1 mM PMSF, and 1 mM EDTA) and centrifuged for 40 minutes at 44000 G and 2° C. Streptomycin sulfate, 10% (w/v), pH 7.0, is added to the supernatant, to a final concentration of 2.5% while stirring on ice, followed by centrifugation for 20 minutes at 27000 G and 2° C. Solid ammonium sulfate (0.243 g/mL, nominally 40%) is then added to the supernatant and the precipitate is recovered by centrifugation for 30 minutes at 27000 G and 2° C. After the precipitate is dissolved in extraction buffer, the extract is iron-reactivated (see Example 9B, below) or directly equilibrated (apo-Pf R2 preparations) in 50 mM Tris-HCl, pH 7.6, 1 mM PMSF, and 1 mM EDTA on a column containing Sephadex G-25 medium. Then about 30 mg of partially purified Pf R2 is loaded onto a 3 mL (3.8×1 cm) DEAE-cellulose column (DE 52, Whatman), previously equilibrated with 10 mM potassium phosphate, pH 7.0, 30 mM KCl, and 1 mM EDTA. The column is washed with 10 mL of the same buffer and Pf R2 is then eluted in 3–4 column volume of 10 mM potassium phosphate, pH 7.0, 70 mM KCl, and 1 mM EDTA. The protein eluate is frozen directly at −70° C. or is recovered by overnight dialysis at 4° C. against saturated ammonium sulfate. The eluated or dialysized protein is centrifuged for 30 minutes at 25000 G and 2° C., is dissolved in 50 mM Tris-HCl, pH 7.6, and is then stored in aliquots at −70° C.

EXAMPLE 58

Enzymatic Activity of Recombinant Pf R1 and R2

A. Recombinant Pf RR Assays

Ribonucleotide reductase activity is assayed at 37° C. using the method of Moore and Peterson, Biochem. 13 2904–2907 (1974) with minor modifications. Briefly, assay mixtures contain 60 mM HEPES, pH 7.6, 26 mM DTT, 7 mM NaF, 5 mM Mg(OAc)$_2$, 3 mM ATP, 0.05 mM FeCl$_3$, and either 10 µg of recombinant Pf R2 prepared by the method of Mann et al. Biochem. 30 1939–1947, or an equivalent volume of buffer A. For CDP reductase assays, 0.05 mM 5-$^3$H]CDP (20 Ci/mol) is added to assay mix, while for GDP reductase assays 1.5 mM dTTP and 0.02 mM [2,8-$^3$H]GDP (45 Ci/mol) is added to a final volume of 100 µl. Reactions are initiated by the addition of recombinant R1 protein, and the assay mixture is incubated at 37° C. for 5–15 min for initial rate determinations. Reactions are quenched by immersion in a boiling water bath for 4 min. Samples are frozen and lyophilized to dryness. Lyophilized samples are reconstituted in 1 ml of 50 mM Tris, pH 8.45 containing 100 mM Mg(OAc)$_2$ (buffer B). Samples are centrifuged at 10,000×G for 10 minutes to precipitate denatured protein. The supernatant is then loaded onto 0.5×5 cm columns of aminophenylboronate (Amicon) which had been pre-equilibrated with 5 ml of buffer B. Deoxynucleoside diphosphates elute in 5 ml (for dCDP) to 12 ml (for dGDP) of buffer B. Unreacted ribonucleoside diphosphate substrates can be quantitatively recovered and columns can be regenerated by treatment with 10 ml of 50 mM sodium citrate, pH 5.9. Radioactivity in aliquots of both buffer B and citrate fractions are determined by liquid scintillation counting.

B. Recombinant Pf R2 Activity

Pf R2 is reactivated by iron and tyrosyl radial regeneration using the procedures described by Mann, et al., Biochem. 30 1939–1947 (1991)). After reactivation, ribonucleotide reductase/Pf R2 activity is determined from the rate of reduction of [$^3$H]-CDP. One unit is defined as the amount of protein which, in the presence of an excess of R1 subunit, catalyzes the formation of one nmol of dCDP/minutes at 37° C. (Engström et al., Biochem., 18 2941–2948 (1979); Ingemarson et al., J. Virol. 63 3769–3776 (1989)). The reactivated Pf R2 protein is assayed in the presence of 15 µg of pure Pf R1 protein, obtained as described in Example 56, above.

EXAMPLE 59

Detecting a Malarial Parasite in a Patient

The presence of a malarial parasite in a patient's blood is detected by a diagnostic polymerase chain reaction (PCR) assay via the following procedures.

Red blood cells suspected of being infected with parasites are collected by centrifugation and lysed to release any malarial parasites that may be present as in Example 56. The DNA is extracted as in Example 56.

A diagnostic PCR assay is then performed on the extracted DNA. Primers complementary to two regions of parasitic DNA corresponding to a portion of SEQ ID NO:1 shows divergence from the hosts' R1 and R2 are used for the diagnostic PCR.

PCR is carried out on Pf DNA in a standard PCR buffer with 1 µM of the upstream primer, 5'-ATT TTC CAT TCC AAA 3' (SEQ ID NO:41), and 1 µM of the downstream primer, 5'-AAA TTC GCT ATT CAG ACA-3' (SEQ ID NO:42). The primers amplify a fragment of DNA about 196 nucleotides in length. Cycling is typically performed for 20–30 cycles at 94° C. for 15 seconds, 50° C. for 15 seconds, and 72° C. for 15 seconds.

Analysis of the PCR products is performed on approximately 10% of the sample by running the sample portion on an 8.0% polyacrylamide. Gels are photographed and transferred to a solid support, e.g., ZetaProbe™ (BioRad), following the manufacturer's recommended procedures to obtain a blot.

As a positive control, a blood sample which is infected by the malarial parasite is subjected to the same procedures as described above. As a negative control, a blood sample which is free of any malarial parasites is subjected to the same procedures as described above.

Radioisotope labeled probes complementary to the portion of the Pf R1 or R2 DNA which the PCR primers will amplify are designed to probe the blots for the parasitic DNA. The blot is exposed to the labelled probe under standard hybridization conditions. Presence of a blot bound to the probe indicates presence of the parasitic DNA.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A purified DNA segment encoding *Plasmodium falciparum* ribonucleotide reductase subunit R1 or R2.

2. A DNA segment comprising a nucleotide sequence encoding a polypeptide according to SEQ ID NO: 2 or SEQ ID NO:4.

3. A DNA segment according to claim 2 wherein said DNA segment comprises a nucleotide sequence according to SEQ ID NO:1, SEQ ID NO:3, or SEQ ID NO:40.

4. A DNA segment according to claim 2 wherein said DNA segment comprises a nucleotide sequence according to SEQ ID NO:40.

5. A plasmid transfer or storage vector comprising a DNA segment according to claim 2.

6. A host cell transformed by a vector comprising a DNA segment according to claim 2, which host cell under culture conditions produces a polypeptide according to SEQ ID NO:2 or SEQ ID NO:4.

7. A plasmid transfer or storage vector comprising a DNA segment according to claim 3.

8. A method for producing a polypeptide having an amino acid sequence according to SEQ ID NO:2 or SEQ ID NO:4, comprising:

cloning into a host cell a DNA segment encoding a polypeptide having the amino acid sequence according to SEQ ID NO:2 or SEQ ID NO:4, culturing said host cell under such conditions so as to produce said polypeptide, and isolating or purifying said polypeptide from the culture media and/or said host cells.

\* \* \* \* \*